(12) United States Patent
Yao et al.

(10) Patent No.: US 10,736,593 B2
(45) Date of Patent: Aug. 11, 2020

(54) X-RAY DIAGNOSTIC APPARATUS AND MEDICAL IMAGE PROCESSING APPARATUS

(71) Applicants: Toshiba Medical Systems Corporation, Otawara-shi (JP); The Johns Hopkins University, Baltimore, MD (US)

(72) Inventors: Jingwu Yao, Buffalo Grove, IL (US); Takuya Sakaguchi, Utsunomiya (JP); Jeff Trost, Baltimore, MD (US); Richard T. George, Baltimore, MD (US); Joao A. C. Lima, Baltimore, MD (US); Omair Yousuf, Baltimore, MD (US)

(73) Assignees: Canon Medical Systems Corporation, Otawara-shi (JP); The Johns Hopkins University, Baltimore, MD (US)

( * ) Notice: Subject to any disclaimer, the term of this patent is extended or adjusted under 35 U.S.C. 154(b) by 1277 days.

(21) Appl. No.: 14/562,220

(22) Filed: Dec. 5, 2014

(65) Prior Publication Data
US 2015/0087956 A1 Mar. 26, 2015

Related U.S. Application Data

(63) Continuation of application No. PCT/JP2013/075791, filed on Sep. 25, 2013, and a
(Continued)

(30) Foreign Application Priority Data

Sep. 12, 2013 (JP) .................................. 2013-189891

(51) Int. Cl.
*A61B 6/00* (2006.01)
*G06T 7/00* (2017.01)
(Continued)

(52) U.S. Cl.
CPC .............. *A61B 6/504* (2013.01); *A61B 6/02* (2013.01); *A61B 6/022* (2013.01); *A61B 6/032* (2013.01);
(Continued)

(58) Field of Classification Search
CPC .. A61B 6/504; A61B 6/02; A61B 6/40; A61B 6/42; A61B 6/469
See application file for complete search history.

(56) References Cited

U.S. PATENT DOCUMENTS 4,400,827 A * 8/1983 Spears .................. A61B 6/481
378/158
5,135,000 A 8/1992 Akselrod et al.
(Continued)

FOREIGN PATENT DOCUMENTS

| CN | 101785679 A | 7/2010 |
|---|---|---|
| JP | 2001-506517 A | 5/2001 |

(Continued)

OTHER PUBLICATIONS

Machine translation from J-Plat Pat of JP 2010-0246725.*
(Continued)

*Primary Examiner* — Katherine L Fernandez
(74) *Attorney, Agent, or Firm* — Oblon, McClelland, Maier & Neustadt, L.L.P.

(57) ABSTRACT

An X-ray diagnostic apparatus according to the embodiment includes an X-ray tube, an X-ray detector, image generating unit generating time-series medical images of vasoganglion in a predetermined organ of a subject, region setting unit setting a first upstream and downstream region of a stenosis location in a first blood vessel in the vasoganglion on the medical images, curve generating unit generating a stenosis upstream and downstream curve indicating a change in pixel value in the time-series based on pixel values included in the
(Continued)

first upstream and downstream region respectively, stenosis index generating unit generating a stenosis index indicating the degree of stenosis in the first blood vessel based on the stenosis upstream and downstream curve, and display unit displaying the stenosis index.

7 Claims, 26 Drawing Sheets

Related U.S. Application Data continuation of application No. 13/626,623, filed on Sep. 25, 2012.

(51) Int. Cl.
*A61B 6/03* (2006.01)
*A61B 6/02* (2006.01)

(52) U.S. Cl.
CPC ............... *A61B 6/40* (2013.01); *A61B 6/42* (2013.01); *A61B 6/4441* (2013.01); *A61B 6/461* (2013.01); *A61B 6/469* (2013.01); *A61B 6/486* (2013.01); *A61B 6/5205* (2013.01); *A61B 6/5217* (2013.01); *A61B 6/541* (2013.01); *G06T 7/0016* (2013.01); *G06T 2207/10016* (2013.01); *G06T 2207/10116* (2013.01); *G06T 2207/20104* (2013.01); *G06T 2207/30104* (2013.01)

(56) References Cited

U.S. PATENT DOCUMENTS

| | | | |
|---|---|---|---|
| 5,357,550 A | 10/1994 | Asahina et al. | |
| 2003/0069508 A1* | 4/2003 | Kawaguchi | A61B 5/02007 600/500 |
| 2003/0191400 A1 | 10/2003 | Shalman et al. | |
| 2005/0065432 A1* | 3/2005 | Kimura | A61B 5/0263 600/420 |
| 2006/0241505 A1 | 10/2006 | Ahmed et al. | |
| 2007/0078352 A1 | 4/2007 | Pijls | |
| 2007/0225614 A1 | 9/2007 | Naghavi et al. | |
| 2008/0107233 A1 | 5/2008 | Sakaguchi et al. | |
| 2008/0317323 A1 | 12/2008 | Kinnstaetter et al. | |
| 2009/0086882 A1* | 4/2009 | Grasruck | A61B 6/481 378/4 |
| 2010/0172556 A1 | 7/2010 | Cohen et al. | |
| 2010/0183207 A1 | 7/2010 | Sakaguchi et al. | |
| 2012/0072190 A1 | 3/2012 | Sharma et al. | |
| 2014/0003687 A1* | 1/2014 | Jou | A61B 6/481 382/130 |
| 2014/0100451 A1* | 4/2014 | Tolkowsky | A61B 6/507 600/424 |

FOREIGN PATENT DOCUMENTS

| | | | |
|---|---|---|---|
| JP | 2005-95340 A | 4/2005 | |
| JP | 2007-007200 A | 1/2007 | |
| JP | 2009-195586 | 9/2009 | |
| JP | 2010-167082 A | 8/2010 | |
| JP | 4537681 B2 | 9/2010 | |
| JP | 2010-246725 A | 11/2010 | |
| WO | WO1998023211 A1 * | 11/1997 | ............... A61B 8/06 |
| WO | WO 98/23211 A1 | 6/1998 | |
| WO | WO 00/53081 A1 | 9/2000 | |
| WO | WO 00/55579 A2 | 9/2000 | |
| WO | WO 01/021057 A2 | 3/2001 | |
| WO | WO 03/022122 A2 | 3/2003 | |
| WO | WO 03/098523 A1 | 11/2003 | |
| WO | WO 2004/019778 A1 | 3/2004 | |
| WO | WO 2011/110817 A2 | 9/2011 | |

OTHER PUBLICATIONS

Molloi et al., "Estimation of coronary artery hyperemic blood flow based on arterial lumen volume using angiographic images", Int J Cardiovascular Imaging, vol. 28, pp. 1-11; Published online Jan. 7, 2011. (Year: 2011).*
Extended European Search Report dated Jun. 9, 2016 in Patent Application No. 13840560.0.
Combined Chinese Office Action and Search Report dated Dec. 1, 2015 in Patent Application No. 201380006619.7 (with English Translation of Category of Cited Documents).
International Search Report dated Nov. 19, 2013 for PCT/JP2013/075791 filed Sep. 25, 2013 with English Translation.
International Written Opinion dated Nov. 19, 2013 for PCT/JP2013/075791 filed Sep. 25, 2013.
Arnoud W.J. van't Hof, et al., "Angiographic Assessment of Myocardial Reperfusion in Patients Treated With Primary Angioplasty for Acute Myocardial Infraction", Circulation 1998; 97: 2302-2306.
C. Michael Gibson, et al. "Relationship of TIMI Myocardial Perfusion Grade to Mortality After Administration of Thrombolytic Drugs", Circulation 2000; 101: 125-130.
Jerry T. Wong et al., "Quantification of fractional flow reserve based on angiographic image data", Int. J. Cardiovasc. Imaging, 2012, 28 (1) , pp. 13-22.
Andrew J. Boyle et al., "Quantitative Automated Assessment of Myocardial Perfusion at Cardiac Catheterization", AM J Cardiol., Oct. 15, 2008;102(8), pp. 980-987.
Michael K. Kyriakidis, et al., "Changes in Phasic Coronary Blood Flow Velocity Profile and Relative Coronary Flow Reserve in Patients with Hypertrophic Obstructive Cardiomyopathy", Circulation, 1997, (96), pp.834-841.
Nico H.J.Pijls, M.D., PHD., et al., "Measurement of Fractional Flow Reserve to Assess the Functional Severity of Coronary-Artery Stenoses", New England Journal of Medicine, Jun. 27, 1996, pp. 1703-708, vol.334,No. 26, Massachusetts Medical Society, MI.
Venu Jasti, MD, et al., "Correlations Between Fractional Flow Reserve and Intravascular ultrasound in Patients with an Ambiguous Left Main Coronary Artery Stenosis", Circulation, Nov. 2,2004, pp. 2831-2836, vol. 110, No. 18, American Heart Association, Inc.
Atsushi Takagi, MD., et al., "Clinical Potential of Intravascular ultrasound for Physiological Assessment of Coronary Stenosis-Relationship Between Quantitative ultrasound Tomography and Pressure-Derived Fractional Flow Reserve ", Circulation, Jul. 20, 1999, pp. 250-255, vol. 100,No. 3, American Heart Association, Inc, TX.
Johannes Rieber, et al., "Cardiac magnetic resonance perfusion imaging for the functional assessment of coronary artery disease: a comparison with coronary angiography and fractional flow reserve", European Heart Journal, UK, May 23, 2006, pp. 1465-1471, vol. 27.
Shigeho Takarada, et al., "An angiographic technique for coronary fractional flow reserve measurement: in vivo validation", The international journal of cardiovascular imaging, Aug. 2012, pp. 535-544.
Nico H.J. Pijls, et al., "Mean transit time for the assessment of myocardial perfusion by videodensitometry", Circulation, Apr. 1990, pp. 1331-1340, vol. 81,No. 4, American Heart Association, Inc. TX.
Office Action dated Jul. 11, 2017 in Japanese Patent Application No. 2013-189891.

* cited by examiner

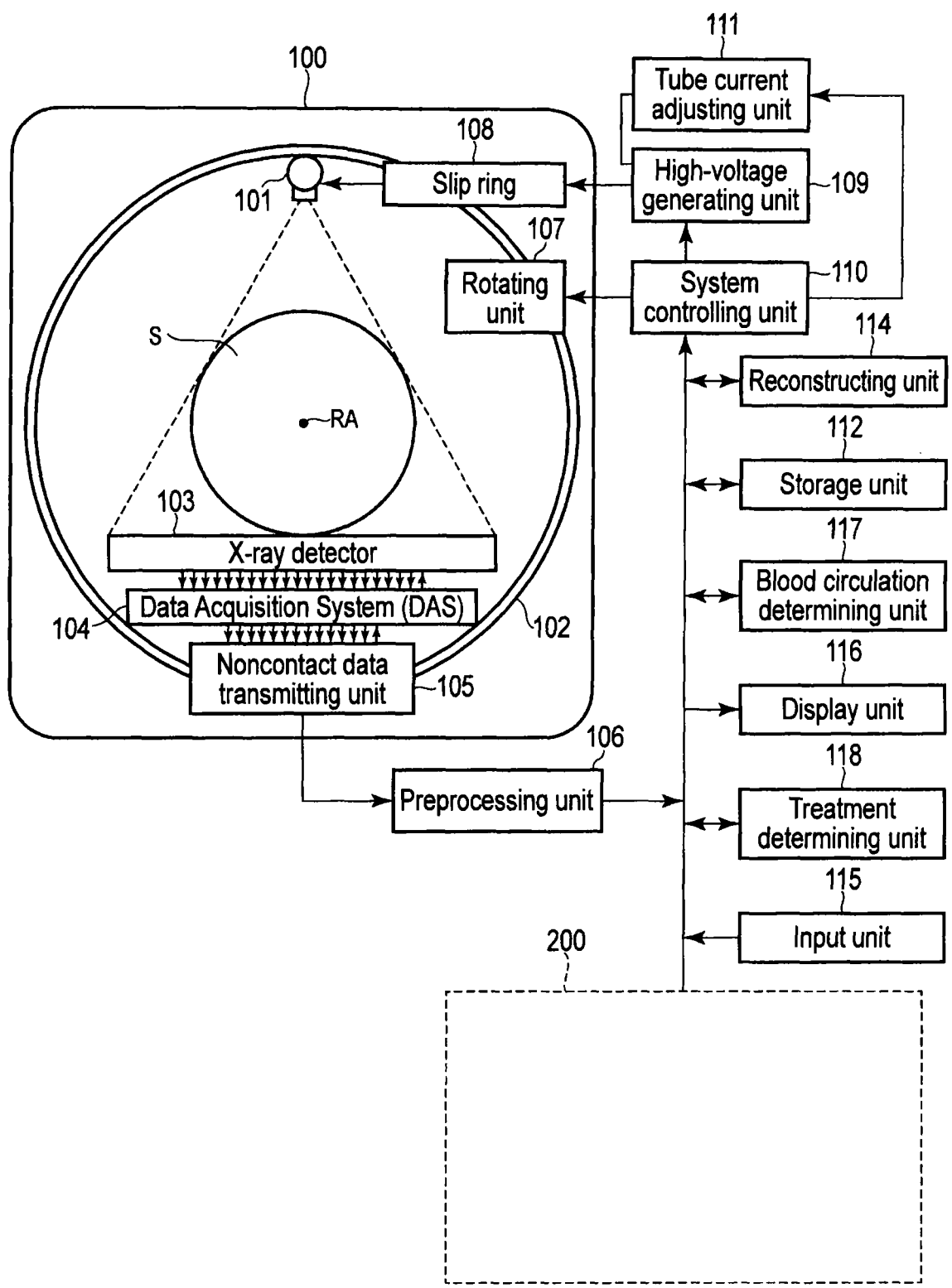
F I G. 2

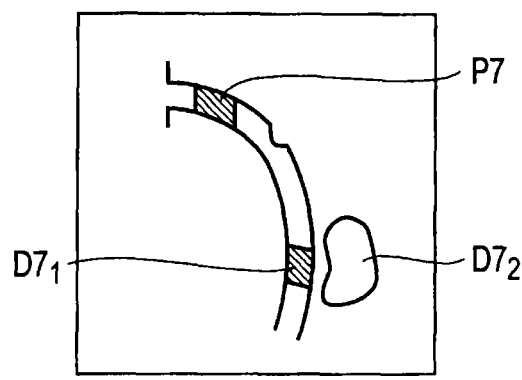
F I G. 9G
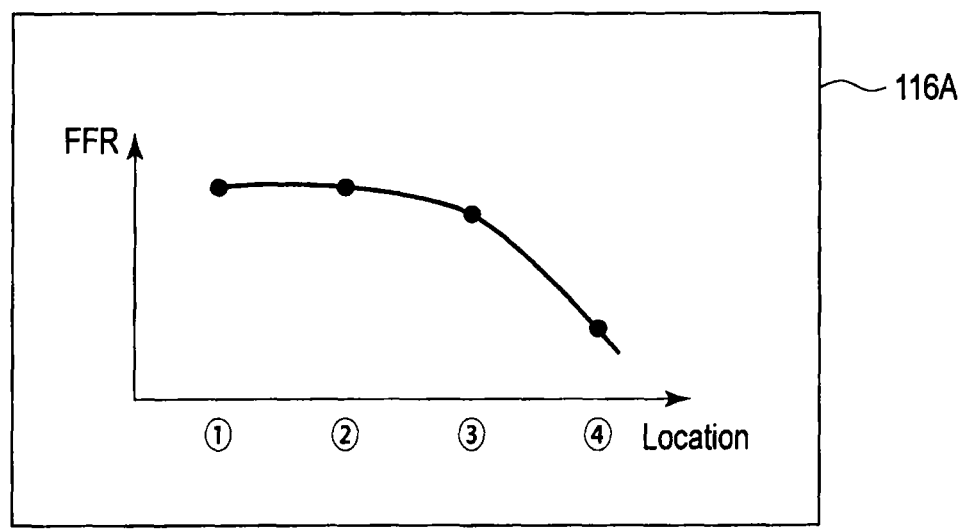
F I G. 10A

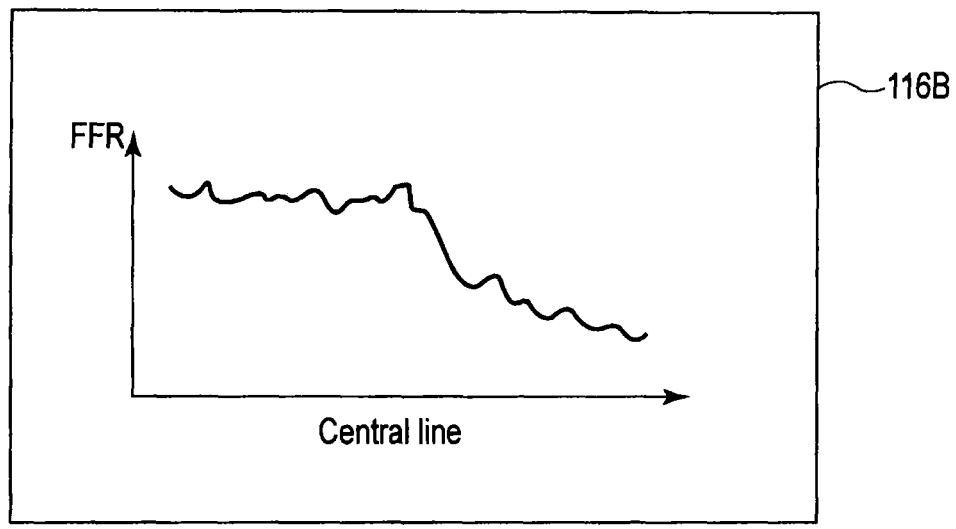
F I G. 10B
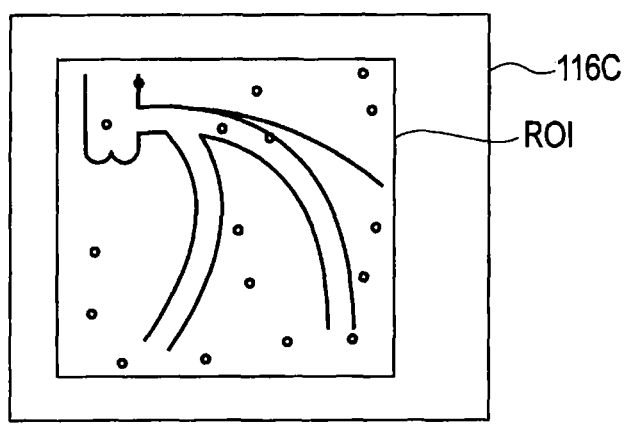
F I G. 10C

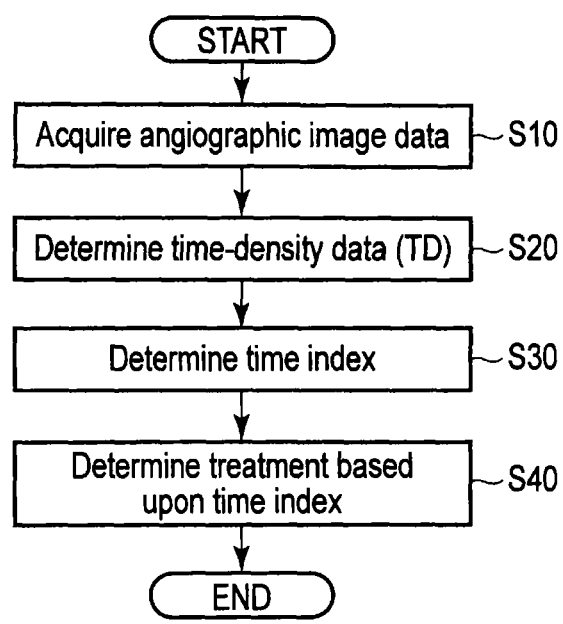
F I G. 11

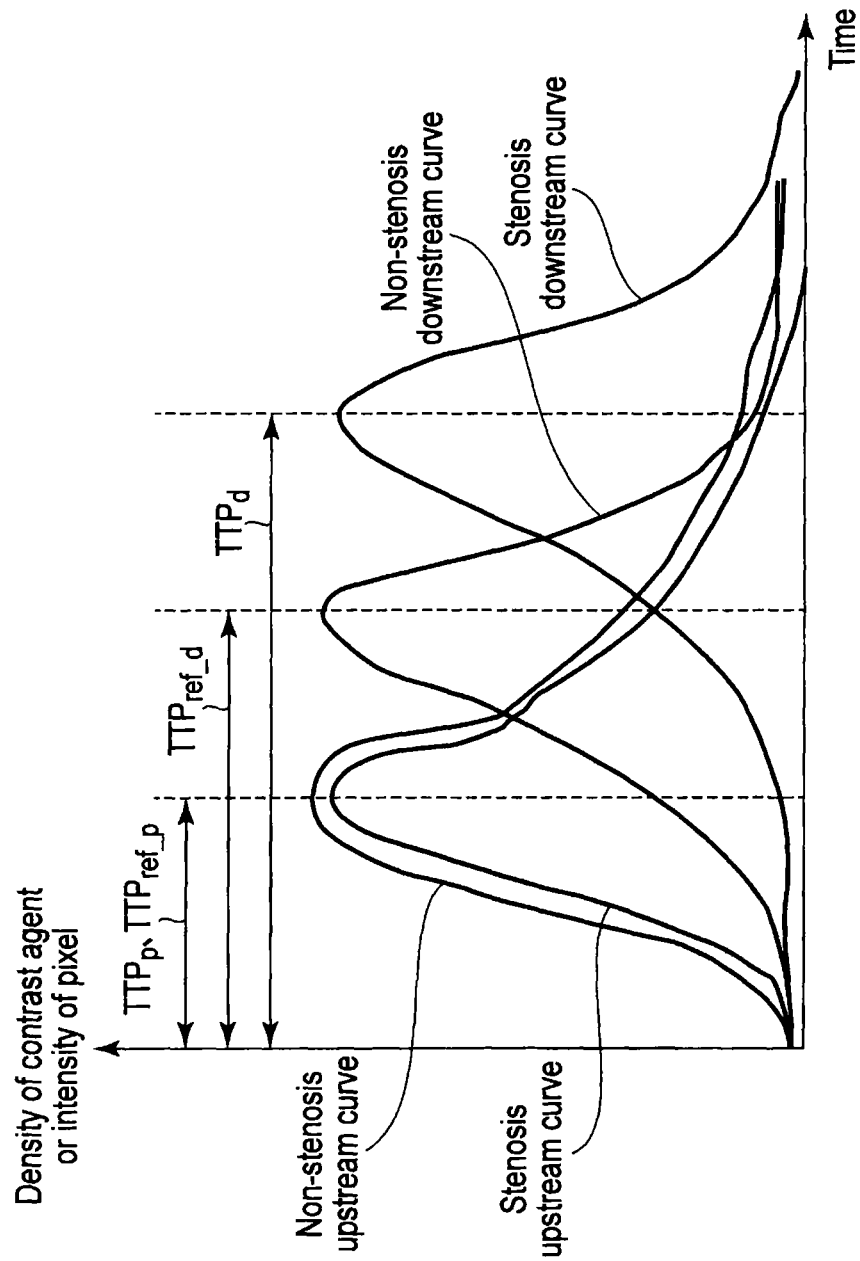
F I G. 18

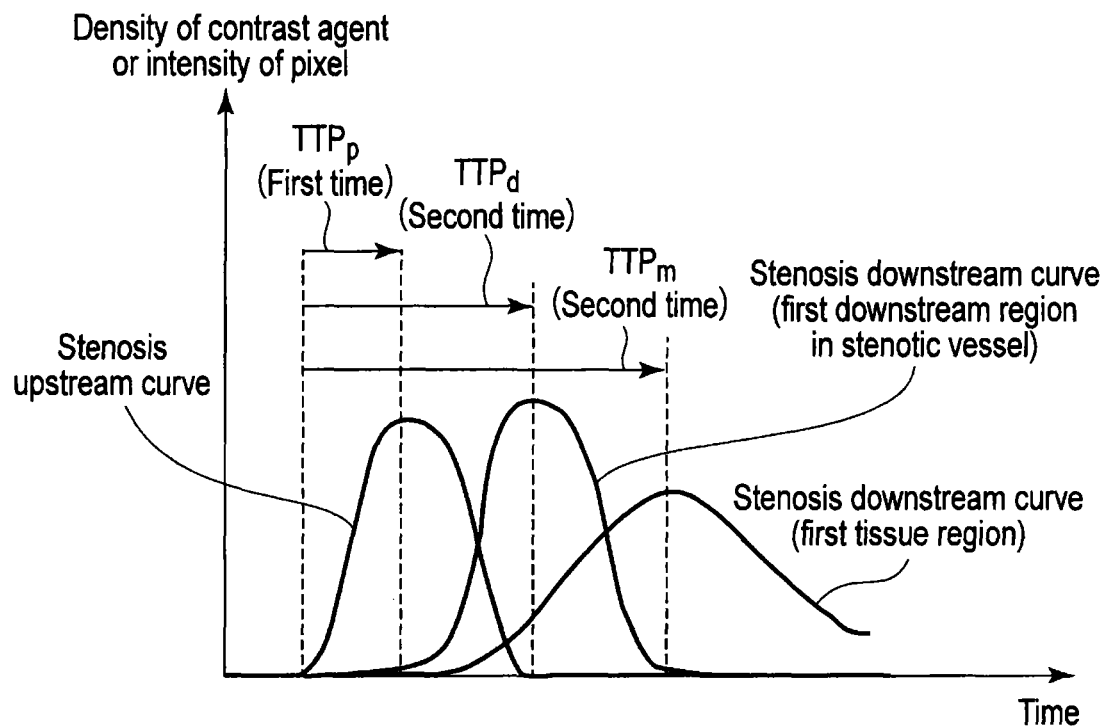
F I G. 23
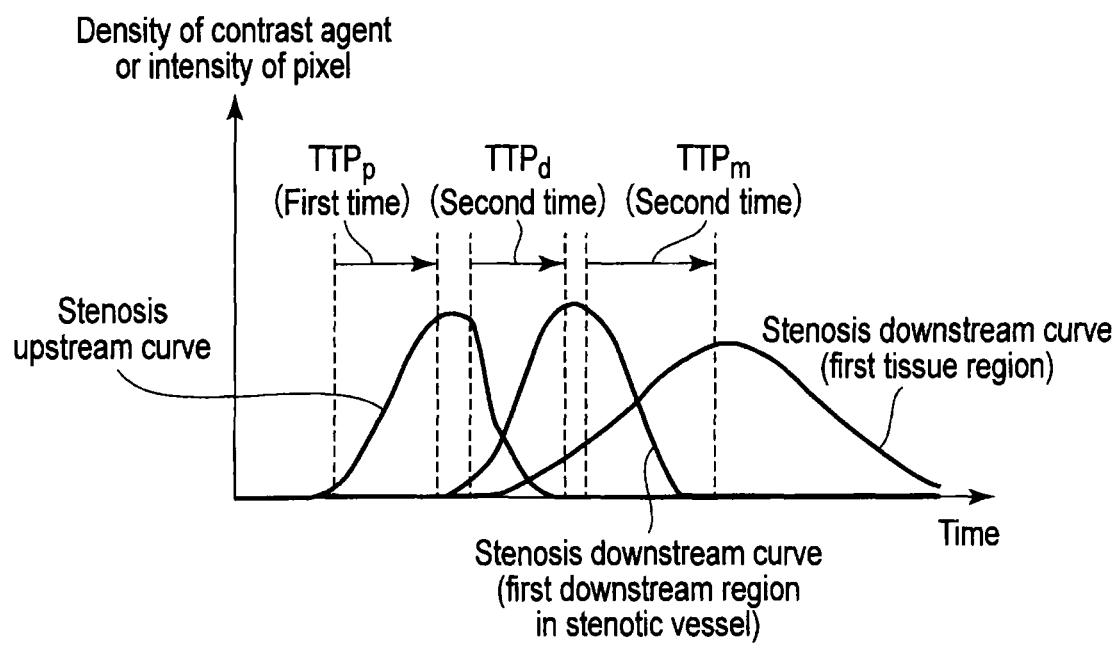
F I G. 24

US 10,736,593 B2

X-RAY DIAGNOSTIC APPARATUS AND MEDICAL IMAGE PROCESSING APPARATUS

CROSS-REFERENCE TO RELATED APPLICATIONS

This application is a Continuation application of PCT Application No. PCT/JP2013/075791, filed Sep. 25, 2013 and based upon and claims the benefit of priority from U.S. application Ser. No. 13/626,623, filed Sep. 25, 2012 and the Japanese Patent Application No. 2013-189891, filed Sep. 12, 2013, the entire contents of all of which are incorporated herein by reference.

FIELD

Embodiments described herein relate generally to an X-ray diagnostic apparatus and a medical image processing apparatus for determining a time-based index (stenosis index) for blood circulation (stenosis in a blood vessel) from imaging data.

BACKGROUND

Relevant prior art has attempted to develop various methods to quantify an extent of blockage of blood circulation. For example, the blockage is often seen as stenosis in a coronary artery, and the extent of blockage is quantified by a predetermined parameter or index. One such widely used index is fractional flow reserve (FFR) for indicating a physiologic significance of coronary artery stenosis.

One area of the prior art attempts directly uses measured pressure data to determine a blockage parameter in a certain blood vessel. By inserting an intracoronary pressure guide wire into a guiding catheter that was introduced to the aorta, the distal coronary pressure and the aortic pressure are measured. After calibration, the pressure guide wire is advanced into coronary artery across stenosis to the most distal artery. As the pressure guide wire tip is kept away from touching the vessel wall, the distal coronary and aortic pressures are recorded simultaneously under maximum coronary vasodilatation. Unfortunately, this measurement technique is an invasive procedure as the pressure wire needs to be inserted into the coronary artery across stenosis and bears some risk.

Another area of the prior art attempts estimates the FFR from a ratio of a coronary blood flow to a total arterial lumen volume based upon angiographic image data. Unfortunately, in order to quantify the total arterial lumen volume and an associated coefficient, complicated processing procedures are required.

Yet another area of the prior art attempts utilizes angiographic image data in order to study blood circulation. In some attempts, time-density curves (TDCs) or time-intensity curves (TICS) are constructed for selected regions of interest (ROIs) from the angiographic image data. Based upon the TDCs or TICs, the blood circulation level is compared among the selected regions. In some of the angiography imaging techniques, although TDCs are generated from the angiographic images, the TDCs reflect density changes in selected regions or tissues rather than individual blood vessels as ROI. On the other hand, a blood flow speed or a rate of change in blood flow speed is evaluated based upon angiographic image data in individual coronary arteries in one angiography imaging technique, and the blood flow speed is determined based upon a distance traveled along a particular artery by the contrast agent over time. That is, the blood flow speed is determined directly from the visual identification of the contrast agent along a blood vessel without the use of time-density data such as TDCs.

In view of the above prior art techniques, it remains desirable to implement a clinical index that is useful in evaluating stenosis in a particular blood vessel so as to objectively determine if a certain medical procedure should be performed on a patient.

BRIEF DESCRIPTION OF THE DRAWINGS

FIG. 2 is a diagram illustrating a multi-slice X-ray CT apparatus or scanner according to the embodiment.

FIG. 9G is a diagram illustrating three exemplary locations for taking intensity measurements on the same branch of a blood vessel such as an artery and in a tissue segment near the artery according to the embodiment.

FIG. 10A is a diagram illustrating a plurality of stenosis indexes (FFRs) corresponding to locations of a plurality of numbers shown in FIG. 9B according to the embodiment.

FIG. 10B is a diagram illustrating a stenosis index (FFR) corresponding to the location of a broken central line shown in FIG. 9C according to the embodiment.

FIG. 10C is a diagram illustrating a display example of stenosis indexes calculated for a plurality of pixels of the angiographic image shown in FIG. 9D according to the embodiment.

FIG. 11 is a flowchart illustrating steps involved in one exemplary process of determining a time-based index ratio for evaluating blood circulation in a predetermined blood vessel or a predetermined tissue segment according to the embodiment.

FIG. 18 is a timing chart illustrating a stenosis upstream curve, a stenosis downstream curve, a non-stenosis upstream curve, and a non-stenosis downstream curve together with a first time ($TTP_p$), a second time ($TTP_d$), a third time ($TTP_{ref\_p}$), and a fourth time ($TTP_{ref\_d}$) according to the first modification of the embodiment.

FIG. 23 is a timing chart illustrating a plurality of TDCs (or a plurality of TICs) respectively corresponding to a first upstream region, a first downstream region in a stenotic vessel, and a first tissue region according to the embodiment.

FIG. 24 is a timing chart illustrating a plurality of TDCs (or a plurality of TICS) respectively corresponding to a first upstream region, a first downstream region in a stenotic vessel, and a first tissue region according to the embodiment.

DETAILED DESCRIPTION

An X-ray diagnostic apparatus according to embodiment includes an X-ray tube, an X-ray detector, an image generating unit, a region setting unit, a curve generating unit, a stenosis index generating unit, and a display unit.

The X-ray tube generates X-rays. The X-ray detector detects X-rays generated by the X-ray tube and transmitted through a subject. The image generating unit generates a plurality of time-series medical images of vasoganglion in a predetermined organ of the subject based on an output from the X-ray detector. The region setting unit sets a first upstream region and a first downstream region of a stenosis location in a first blood vessel in the vasoganglion on the medical images. The curve generating unit generates a stenosis upstream curve indicating a change in pixel value in the time-series based on a plurality of pixel values included in the first upstream region, and generate a stenosis downstream curve indicating a change in pixel value in the time-series based on a plurality of pixel values included in the first downstream region. The stenosis index generating unit generates a stenosis index indicating a degree of stenosis in the first blood vessel based on the stenosis upstream curve and the stenosis downstream curve. The display unit displays the stenosis index.

Figure 1:
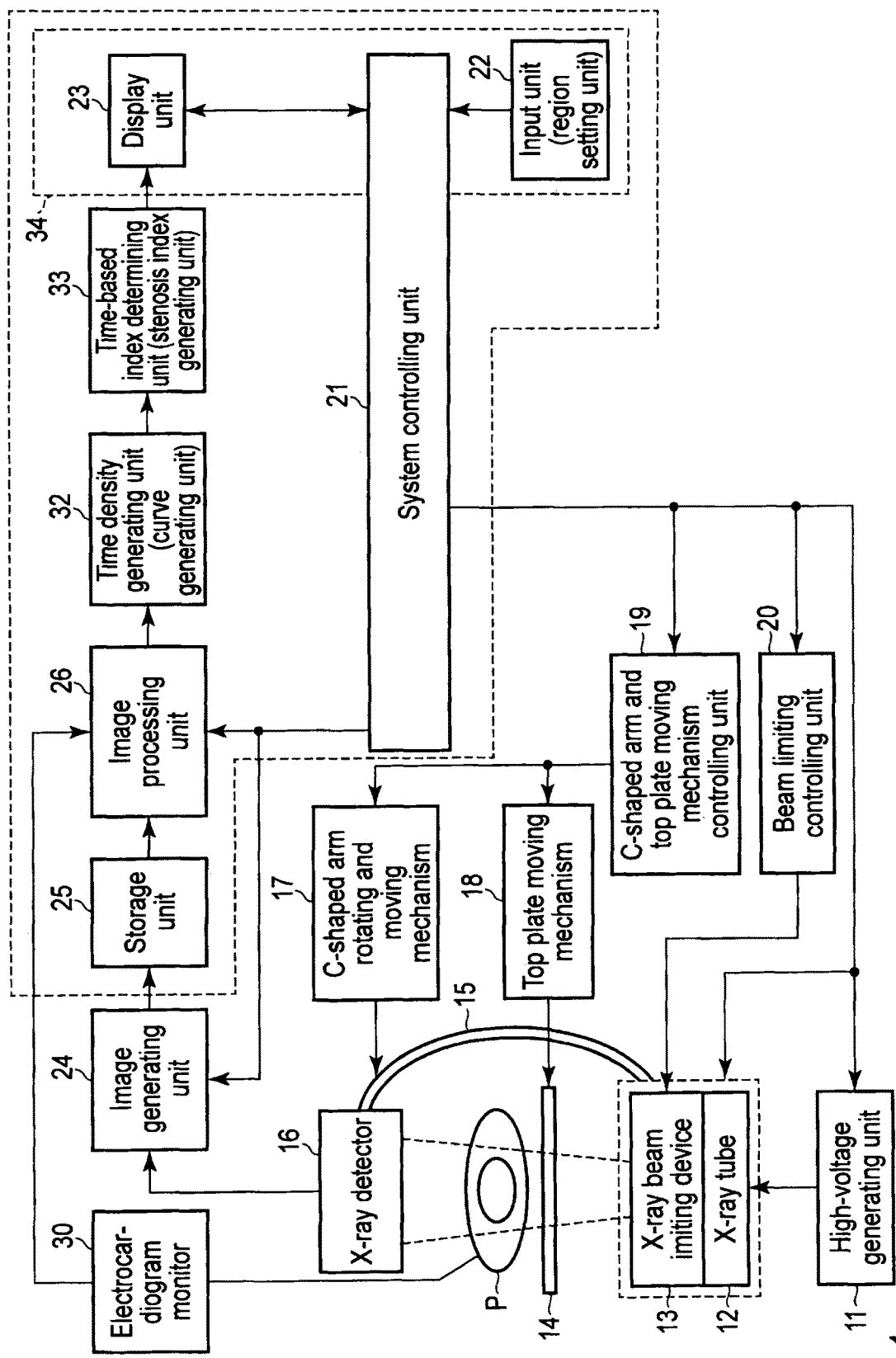
FIG. 1 is a diagram illustrating an example of an X-ray diagnostic apparatus according to an embodiment.

Referring now to the drawings, wherein like reference numerals designate corresponding structures throughout the views, and now referring to FIG. 1, a diagram illustrates one embodiment of an X-ray diagnostic apparatus for evaluating blood circulation (stenosis) in a blood vessel according to the current invention. The X-ray diagnostic apparatus includes a high-voltage generating unit 11, an X-ray tube 12, an X-ray beam limiting device 13, a top plate 14, a C-shaped arm 15, an X-ray detector 16, a C-shaped arm rotating and moving mechanism 17, a top plate moving mechanism 18, a C-shaped-arm and top-plate moving mechanism controlling unit 19, a beam-limiting controlling unit 20, a system controlling unit 21, an input unit 22, a display unit 23, an image generating unit 24, a storage unit 25, and an image processing unit 26. In a certain embodiment, a user interface unit 34 includes the input unit 22, the display unit 23 and a certain portion of the system controlling unit 21. Further, as shown in FIG. 1, the X-ray diagnostic apparatus according to the first embodiment is configured so that an electrocardiogram monitor 30 attached to an examined subject P is connected to the image processing unit 26.

In general, X-ray transmission images are generated in the following manner. The X-ray beam limiting device 13 selectively irradiates a region of interest including the heart of the subject P with X-ray beams generated by the X-ray tube 12. The X-ray detector 16 includes a plurality of X-ray detecting elements for detecting X-ray beams that have passed through the subject P, converting the detected X-ray beams into an electrical signal, storing the electrical signal, and transmitting the stored electrical signal to the image generating unit 24. Thus, an image data acquiring unit includes at least the X-ray detector for acquiring imaging data (angiographic image data) indicating blood circulation in a region of interest (ROI) including at least the interior of a predetermined risk blood vessel. The image generating unit 24 generates X-ray transmission images based upon the electrical signal and stores the generated X-ray transmission images in the storage unit 25. The input unit (region setting unit) 22 includes one or more of devices such as a touch panel, a touch screen, a mouse, a keyboard, a button, a trackball, and a joystick that are used by an operator like a medical doctor or a technologist who operates the X-ray diagnostic apparatus for the purpose of inputting various types of commands. One of the commands is to specify a region of interest using a particular user interface unit in the input unit 22. The input unit 22 transfers the commands that have been received from the operator to the system controlling unit 21.

In further detail, the user interface unit 34 in one embodiment includes the display unit 23 and the input unit 22 for providing certain features according to this embodiment. Using the user interface unit 34 such as a Graphical User Interface (GUI), the operator manually specifies a ROI in the displayed image for evaluating blood circulation in a blood vessel or a tissue region according to this embodiment. The display unit 23 indicates a contour of an input region or a ROI that has been specified for evaluating blood circulation (stenosis) in a manner that is fused with the displayed image. In one embodiment, the display unit 23 also displays the blood circulation (stenosis) evaluation results in numerical values of a predetermined time-based index and/or in a predetermined graphical form. In one predetermined graphical form, the values of the time-based index (a stenosis index corresponding to an FFR (to be described later)) are plotted in the Y axis while the selected regions (ROIs) are plotted in the X-axis, as illustrated in FIG. 10A. In another predetermined graphical form, the values of the time-based index (stenosis index (FFR)) are plotted in the Y axis while the selected points along a predetermined line in a ROI are plotted in the X axis, as illustrated in FIG. 10B. In yet another predetermined graphical form, the values of the time-based index (stenosis index (FFR)) are mapped in the X-Y coordinate with respect to a selected structure such as a blood vessel, as illustrated in FIG. 10C.

Still referring to FIG. 1, the above embodiment of the X-ray diagnostic apparatus evaluates blood circulation (the degree of stenosis) in a blood vessel according to this embodiment. The electrocardiogram monitor 30 obtains an electrocardiogram (ECG) waveform of the subject P and transmits the obtained electrocardiogram waveform together with time and movement information to the image processing unit 26. The image processing unit 26 is connected to the image data acquiring unit for performing various processes such as ECG gating, motion compensation and background subtraction on the imaging data. A time density generating unit (curve generating unit) 32 is connected to the image processing unit 26 for generating time-density data (time-density curve) in the ROI from the imaging data (angiographic image data) at a proximal location and a distal location at least with respect to the predetermined risk blood vessel. In general, the proximal location is proximal to a suspected stenosis in the predetermined risk blood vessel while the distal location is distal to the suspected stenosis. Furthermore, a time-based index determining unit (stenosis index generating unit) 33 is connected to the time density generating unit (curve generating unit) 32 for determining based upon the time-density data a time-based index (stenosis index) for evaluating a level of the blood circulation (stenosis) between the proximal location and the distal location in the ROI.

The C-shaped arm 15 supports the X-ray tube 12, the X-ray beam limiting device 13, and the X-ray detector 16 while the C-shaped arm rotating and moving mechanism 17 rotates and moves the C-shaped arm 15 under the control of the C-shaped-arm and top-plate moving mechanism controlling unit 19.

In summary, the X-ray diagnostic apparatus according to the first embodiment generates X-ray transmission images by irradiating, with the X-ray beams, the heart of the subject P in which a contrast agent has been injected into the coronary arteries. Further, the X-ray diagnostic apparatus according to the first embodiment determines blood circulation (stenosis) levels in regions of interest such as a blood vessel or tissue regions based upon a predetermined time-based index (stenosis index) such as a fractional flow reserve (FFR).

Generation of a stenosis index will be described in detail below.

Figure 12:
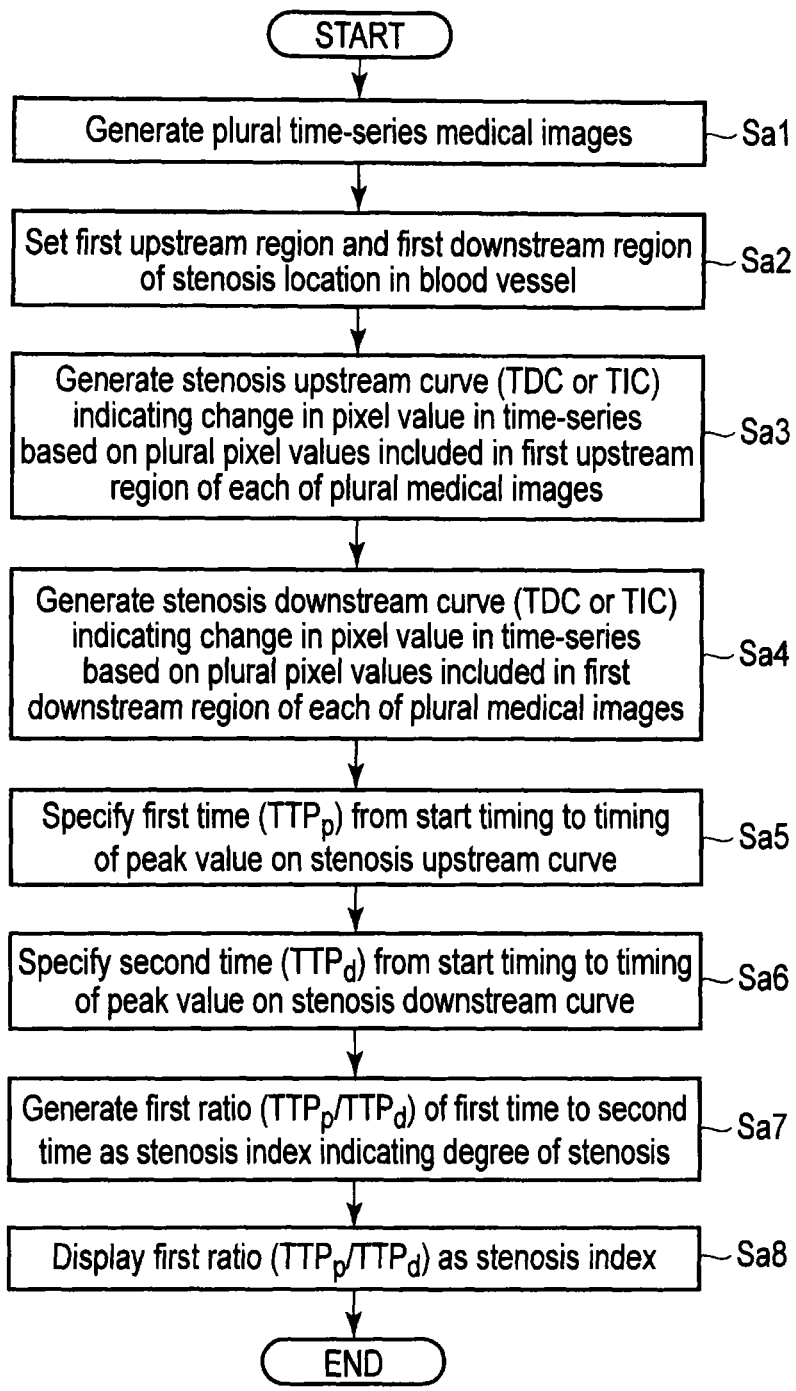
FIG. 12 is a flowchart illustrating an example of a procedure of generating a stenosis index according to the embodiment.

FIG. 12 is a flowchart illustrating an example of a procedure of generating a stenosis index.

With a series of X-ray imaging operations on the subject, the image generating unit 24 generates a plurality of time-series medical images (angiographic images) of vasoganglion in a predetermined organ of the subject (step Sa1). The generated angiographic images are displayed on the display unit 23. In response to a command from the operator via the input unit 22, the region setting unit sets a first upstream region (a proximal location of a branching portion of a first blood vessel) in the upstream portion of a stenosis location in a blood vessel (first blood vessel) of the vasoganglion on the displayed angiographic images. The first blood vessel is a blood vessel including stenosis in the vasoganglion. In response to a command from the operator via the input unit 22, the region setting unit sets a first downstream region (a distal location of the branching portion of the blood vessel) in the downstream portion of the stenosis location in the first blood vessel on the displayed angiographic images (step Sa2).

Figure 9A:
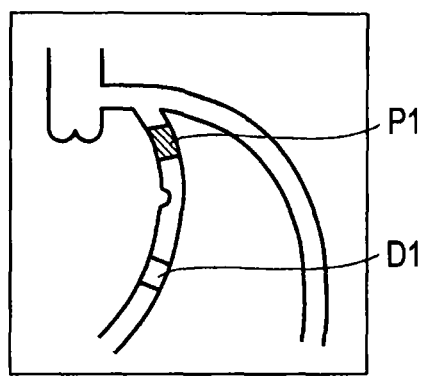
FIG. 9A is a diagram illustrating a first pair of exemplary locations for taking intensity measurements on the same branch of a blood vessel such as an artery according to the embodiment.

FIG. 9A is a diagram illustrating an example of the set first upstream region and the set first downstream region. In FIG. 9A, reference symbol P1 denotes a first upstream region; and D1, a first downstream region.

The curve generating unit 32 generates a stenosis upstream curve indicating a change in pixel value in a time-series based upon a plurality of pixel values included in the first upstream region of each of the plurality of medical images (angiographic images) (step Sa3). The curve generating unit 32 also generates a stenosis downstream curve indicating a change in pixel value in a time-series based upon a plurality of pixel values included in the first downstream region of each of the plurality of medical images (angiographic images) (step Sa4). The stenosis upstream curve and the stenosis downstream curve are curves (TDCs (Time-Density Curves) or TICS (Time-Intensity Curves)) each indicating a change in pixel value, that is, density of the contrast agent (or intensity of a pixel value) with time.

The stenosis index generating unit 33 generates a stenosis index indicating the degree of stenosis in a blood vessel (first blood vessel) including stenosis based upon the stenosis upstream curve and the stenosis downstream curve. More specifically, the stenosis index generating unit 33 specifies a first time ($TTP_p$) from the start timing of the stenosis upstream curve to the timing of its peak value (TTP (Time-To-Peak)) (step Sa5). The stenosis index generating unit 33 specifies a second time ($TTP_d$) from the start timing of the stenosis downstream curve to the timing of its peak value (TTP) (step Sa6).

Figure 13:
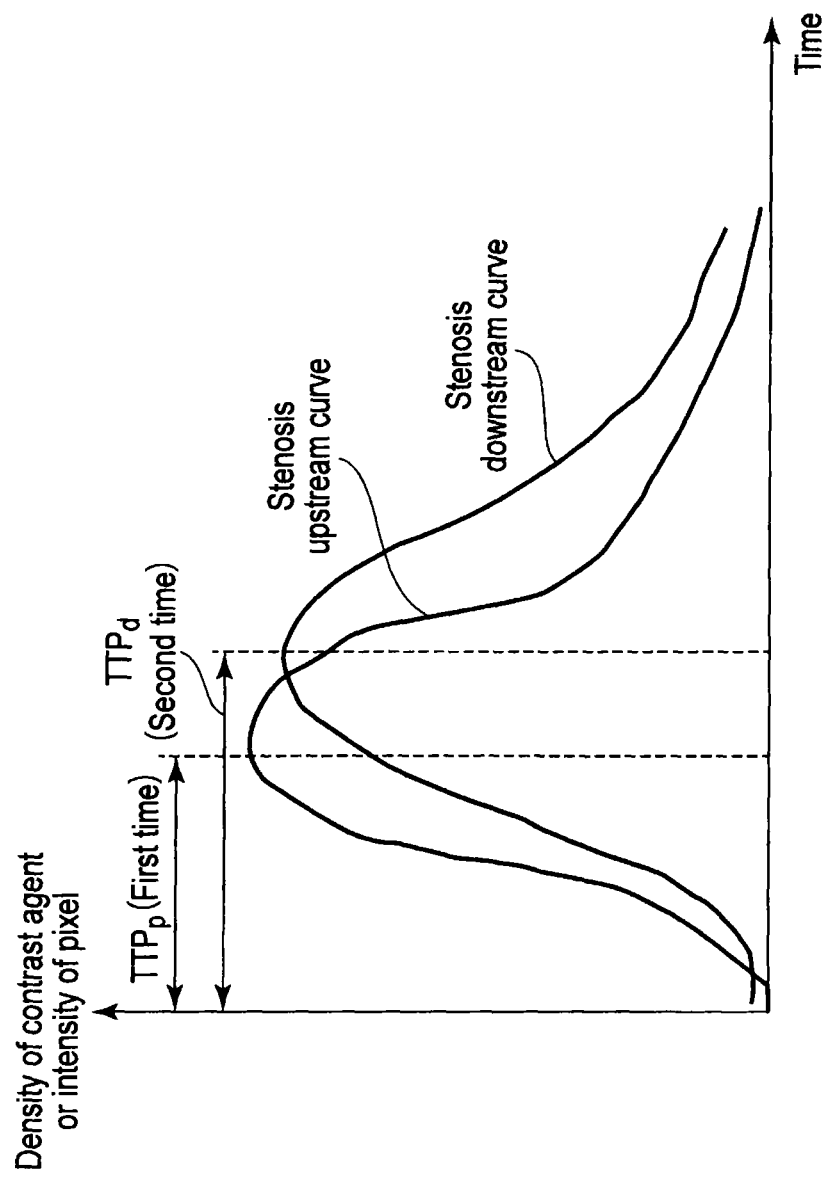
FIG. 13 is a timing chart illustrating a stenosis upstream curve and a stenosis downstream curve together with a first time ($TTP_p$) and a second time ($TTP_d$) according to the embodiment.

FIG. 13 is a timing chart illustrating the stenosis upstream curve and the stenosis downstream curve together with the first time ($TTP_p$) and the second time ($TTP_d$). As shown in FIG. 13, the peak value of the TDC (TIC) in the first upstream region appears earlier than that of the TDC (TIC) in the first downstream region. Furthermore, the peak value of the TDC (TIC) in the first upstream region is larger than that of the TDC (TIC) in the first downstream region.

The stenosis index generating unit 33 generates a ratio (first ratio) between the first time and the second time as a stenosis index indicating the degree of stenosis in the blood vessel. More specifically, the stenosis index generating unit 33 generates the ratio ($TTP_p/TTP_d$) of the first time to the second time as a stenosis index (step Sa7). The stenosis index generating unit 33 outputs the generated stenosis index to the display unit 23. The ratio ($TTP_p/TTP_d$) of the first time to the second time is a stenosis index corresponding to a fractional flow reserve (FFR).

The display unit 23 displays the stenosis index generated by the stenosis index generating unit 33 (step Sa8).

Note that the stenosis index generating unit 33 may specify the volume ($V_p$) of the blood vessel portion of the first blood vessel in the first upstream region and the volume ($V_d$) of the blood vessel portion of the first blood vessel in the first downstream region. In this case, the stenosis index generating unit 33 may generate the volume ratio ($V_p/V_d$) of the volume ($V_p$) of the blood vessel portion in the first upstream region to the volume ($V_d$) of the blood vessel portion in the first downstream region as a stenosis index.

Figure 14:
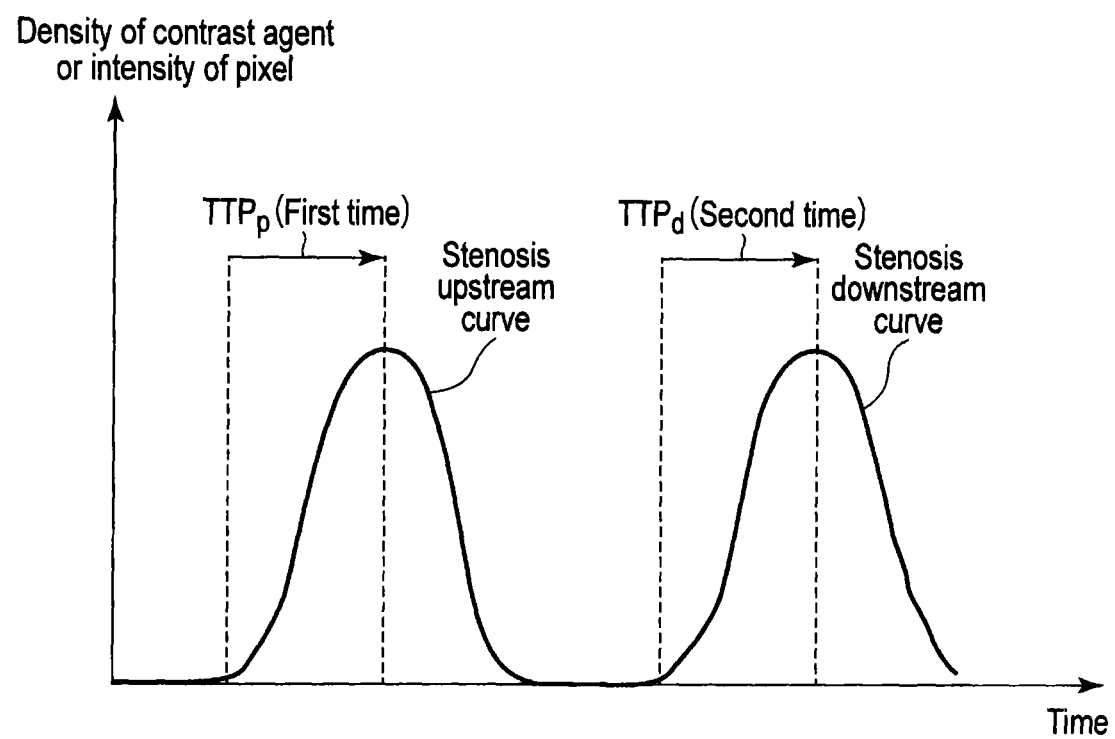
FIG. 14 is a timing chart illustrating a case in which the time from the start timing of the stenosis downstream curve to the timing of its peak value (TTP) is specified as the second time ($TTP_d$) according to the embodiment.

Note that the stenosis index generating unit 33 may generate a stenosis index as follows. For example, the stenosis index generating unit 33 may specify the time from the start timing of the stenosis upstream curve to the timing of the peak value (TTP) of the stenosis downstream curve as the second time ($TTP_d$). FIG. 14 is a timing chart illustrating a case in which the time from the start timing of the stenosis downstream curve to the timing of its peak value (TTP) as the second time ($TTP_d$). Instead of $TTP_d$ of the timing chart shown in FIG. 13, the stenosis index generating unit 33 specifies the second time ($TTP_d$), as illustrated in the timing chart shown in FIG. 14.

Figure 15:
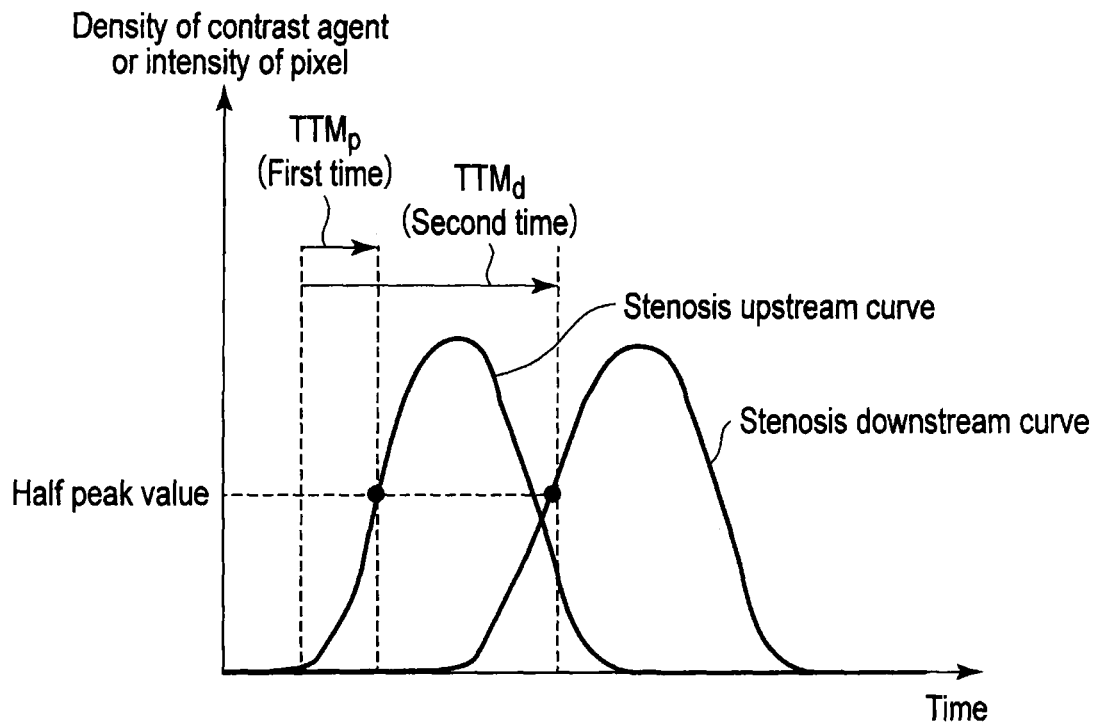
FIG. 15 is a timing chart illustrating $TTM_p$ of the stenosis upstream curve and $TTM_d$ of the stenosis downstream curve according to the embodiment.

Furthermore, instead of the first time ($TTP_p$), the stenosis index generating unit 33 may specify the time from the start timing of the stenosis upstream curve to the timing of half the peal value (or mean value) of the stenosis upstream curve as a first time ($TTM_p$ (Time-To-Mean)). In this case, instead of the second time ($TTP_d$), the stenosis index generating unit 33 may specify the time from the start timing of the stenosis upstream curve to the timing of half the peak value (or mean value) of the stenosis downstream curve as a second time ($TTM_d$ (Time-To-Mean)). At this time, the stenosis index generating unit 33 generates the ratio ($TTM_p/TTM_d$) of the first time ($TTM_p$) to the second time ($TTM_d$) as a stenosis index. FIG. 15 is a timing chart illustrating $TTM_p$ of the stenosis upstream curve and $TTM_d$ of the stenosis downstream curve.

Figure 16:
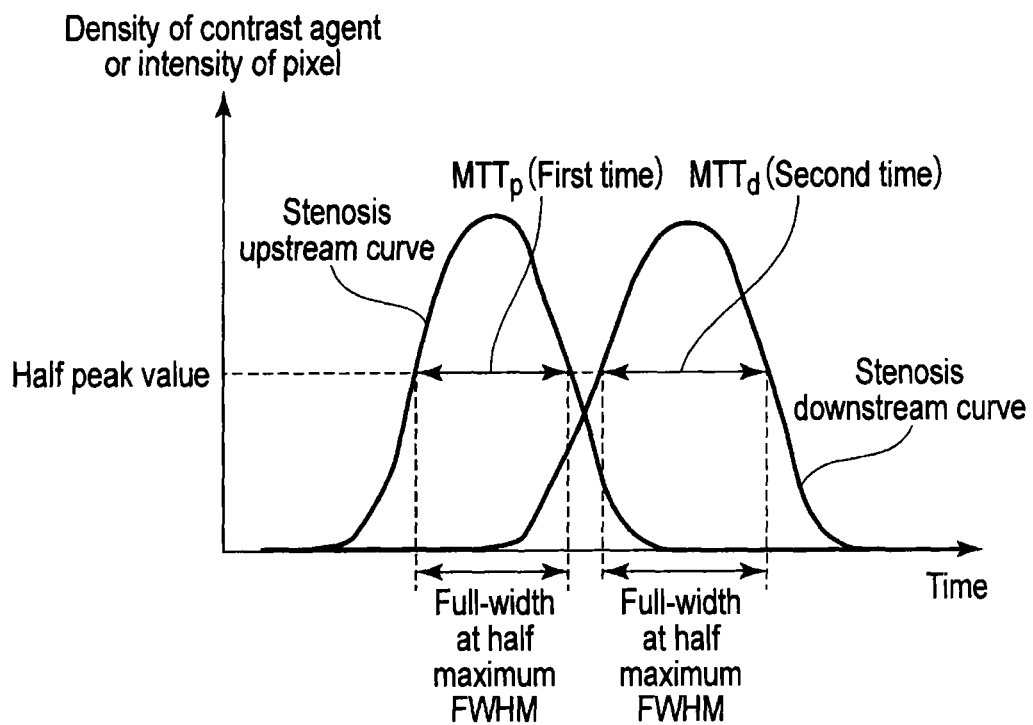
FIG. 16 is a timing chart illustrating $MTT_p$ of the stenosis upstream curve and $MTT_d$ of the stenosis downstream curve according to the embodiment.

The stenosis index generating unit 33 may specify, as a first time, a mean transit time (MTT) during which the contrast agent passes through the first upstream region. That is, for the stenosis upstream curve, the stenosis index generating unit 33 specifies, for example, the time (for example, FWHM (Full Width at Half Maximum)) between the timings of the average value of the peak value (or half the peak value) as a first time ($MTT_p$). In this case, the stenosis index generating unit 33 specifies, as a second time, a mean transit time (MTT) during which the contrast agent passes through the first downstream region. That is, for the stenosis downstream curve, the stenosis index generating unit 33 specifies, for example, the time (for example, FWHM) between the timings of the average value of the peak values as a second time ($MTT_d$). In this case, the stenosis index generating unit 33 generates the ratio ($MTT_p/MTT_d$) of the first time ($MTT_p$) to the second time ($MTT_d$) as a stenosis index. FIG. 16 is a timing chart illustrating MTT of the stenosis upstream curve and $MTT_d$ of the stenosis downstream curve.

Figure 17:
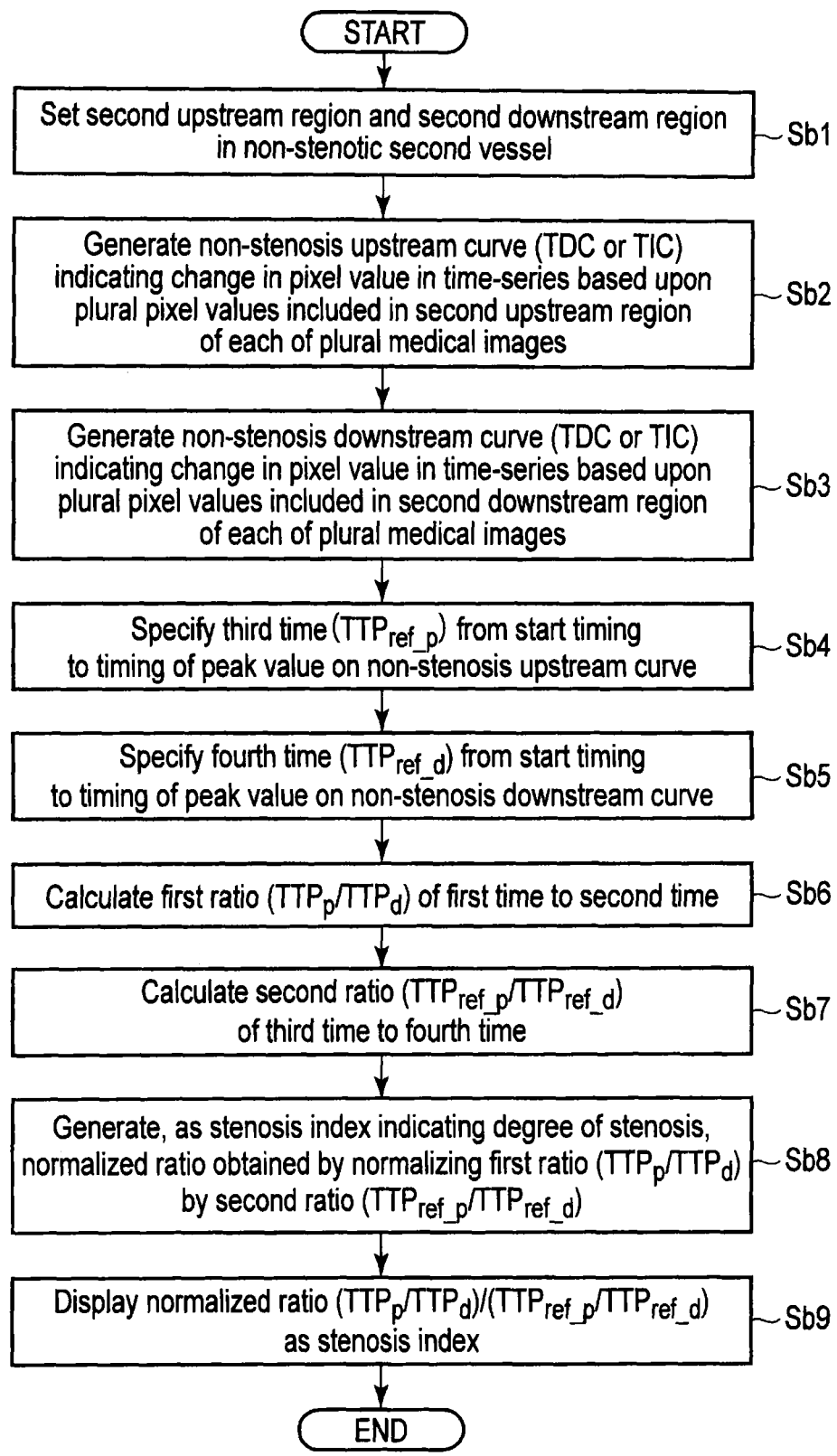
FIG. 17 is a flowchart illustrating an example of a procedure of generating a stenosis index according to the first modification of the embodiment.

In the first modification of this embodiment, a stenosis index may be generated as follows. FIG. 17 is a flowchart illustrating an example of a procedure of generating a stenosis index according to the first modification.

With a series of X-ray imaging operations on the subject, the image generating unit 24 generates a plurality of time-series medical images (angiographic images) of vasoganglion in a predetermined organ of the subject. The generated angiographic images are displayed on the display unit 23. In response to a command from the operator via the input unit 22, the region setting unit sets a second upstream region and a second downstream region in a second non-stenotic (reference) vessel (to be referred to as a non-stenotic vessel hereinafter) in vasoganglion on the displayed angiographic images (step Sb1). More specifically, the second upstream region is set in the non-stenotic vessel so that the distance between the first upstream region and the branching portion of the non-stenotic vessel and the first blood vessel (to be referred to as a stenotic vessel hereinafter) in which the first upstream region is set becomes substantially equal to that between the branching portion and the second upstream region.

In response to a command from the operator via the input unit 22, the region setting unit sets a second downstream region in the downstream portion of the non-stenotic vessel on the displayed angiographic images. More specifically, the second downstream region is set in the non-stenotic vessel so that the distance between the branching portion and the first downstream region becomes substantially equal to that between the branching portion and the second downstream region.

Furthermore, the second upstream region and the second downstream region are set in the non-stenotic vessel so that the distance between the second upstream region and the second downstream region becomes equal to that between the first upstream region and the first downstream region.

Figure 5A:
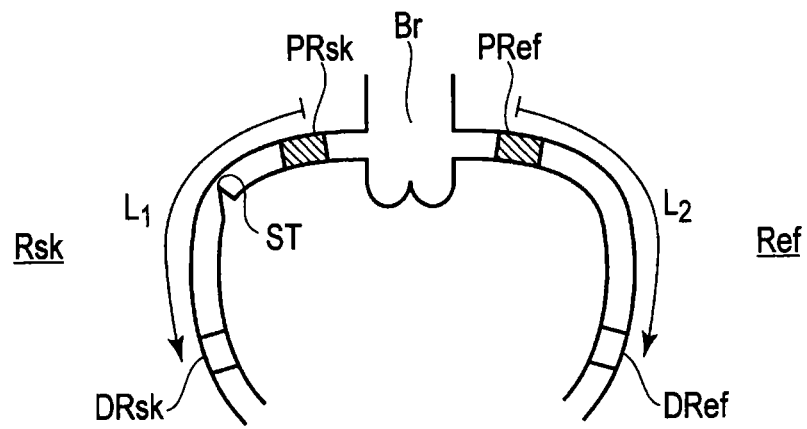
FIG. 5A is a diagram illustrating exemplary measurement locations for determining time-density data from the angiographic image data as acquired in a region of interest that includes a predetermined risk artery and a predetermined reference artery according to the embodiment.
Figure 5B:
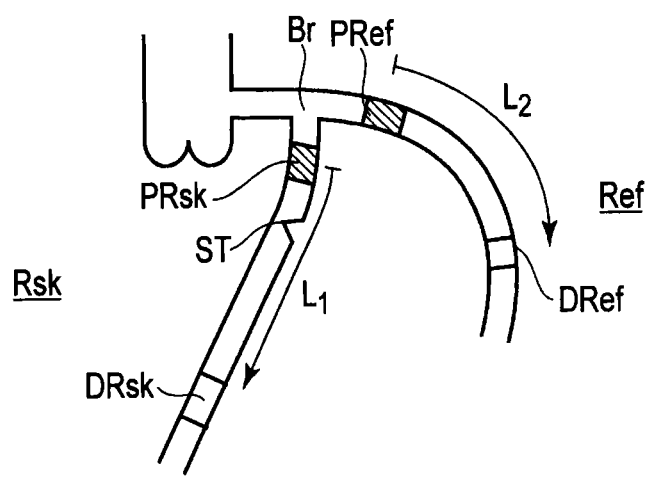
FIG. 5B is a diagram illustrating exemplary measurement locations for determining time-density data from the angiographic image data as acquired in a region of interest that includes a predetermined risk artery and a predetermined reference artery that have different shapes according to the embodiment.

FIG. 5B is a diagram illustrating a first upstream region and a first downstream region which are set in a stenotic vessel and a second upstream region and a second downstream region which are set in a non-stenotic vessel. Referring to FIG. 5B, reference symbol PRsk denotes a first upstream region; DRsk, a first downstream region; ST, a stenosis location in the stenotic vessel; PRef, a second upstream region; and DRef, a second downstream region. As shown in FIG. 5B, a distance L1 between the first upstream region and the first downstream region is almost equal to a distance L2 between the second upstream region and the second downstream region.

The curve generating unit 32 generates a non-stenosis upstream curve indicating a change in pixel value in a time-series based upon a plurality of pixel values included in the second upstream region of each of the plurality of medical images (angiographic images) (step Sb2). The curve generating unit 32 also generates a non-stenosis downstream curve indicating a change in pixel value in a time-series based upon a plurality of pixel values included in the second downstream region of each of the plurality of medical images (angiographic images) (step Sb3). The non-stenosis upstream curve and the non-stenosis downstream curve are curves (TDCs (Time-Density Curves) or TICs (Time-Intensity Curves)) each indicating a change in pixel value, that is, density of the contrast agent (or intensity of a pixel value) with time.

The stenosis index generating unit 33 generates a stenosis index indicating the degree of stenosis in the first blood vessel (stenotic vessel) based upon the stenosis upstream curve, stenosis downstream curve, non-stenosis upstream curve, and non-stenosis downstream curve. More specifically, the stenosis index generating unit 33 specifies a third time ($TTP_{ref\_p}$) from the start timing of the non-stenosis upstream curve to the timing of its peak value (TTP (Time-To-Peak)) (step Sb4). The stenosis index generating unit 33 specifies a fourth time ($TTP_{ref\_d}$) from the start timing of the stenosis downstream curve to the timing of its peak value (TTP) (step Sb5).

FIG. 18 is a timing chart illustrating the stenosis upstream curve, stenosis downstream curve, non-stenosis upstream curve, and non-stenosis downstream curve together with the first time ($TTP_p$), second time ($TTP_d$), third time ($TTP_{ref\_p}$), and fourth time ($TTP_{ref\_d}$). As shown in FIG. 18, the peak value of the stenosis downstream curve (TDC (TIC) in the first downstream region) appears later than that of the non-stenosis downstream curve (TDC (TIC) in the second downstream region) due to stenosis in the blood vessel.

The stenosis index generating unit 33 calculates a first ratio between the first time and the second time. The stenosis index generating unit 33 calculates a second ratio between the third time and the fourth time. The stenosis index generating unit 33 generates a stenosis index indicating the degree of stenosis in a stenotic vessel (first blood vessel) based upon the first ratio and second ratio. The stenosis index generating unit 33 outputs the generated stenosis index to the display unit 23.

More specifically, the stenosis index generating unit 33 calculates the ratio ($TTP_p/TTP_d$) of the first time to the second time as the first ratio (step Sb6). The stenosis index generating unit 33 calculates the second ratio ($TTP_{ref\_p}/TTP_{ref\_d}$) of the third time to the fourth time (step Sb7). The stenosis index generating unit 33 generates, as a stenosis index in the stenotic vessel, a normalized ratio (($TTP_p/TTP_d$)/($TTP_{ref\_p}/TTP_{ref\_d}$)) obtained by normalizing the first ratio by the second ratio (step Sb8). The display unit 23 displays the normalized ratio (($TTP_p/TTP_d$)/($TTP_{ref\_p}/TTP_{ref\_d}$)) as a stenosis index (step Sb9).

Note that the stenosis index generating unit 33 may generate a volume ratio ($V_{ref\_p}/V_{ref\_d}$) of the blood vessel volume ($V_{ref\_p}$) of the second upstream region to the blood vessel volume ($V_{ref\_d}$) of the second downstream region as the volume ratio ($V_p/V_d$).

Figure 19:
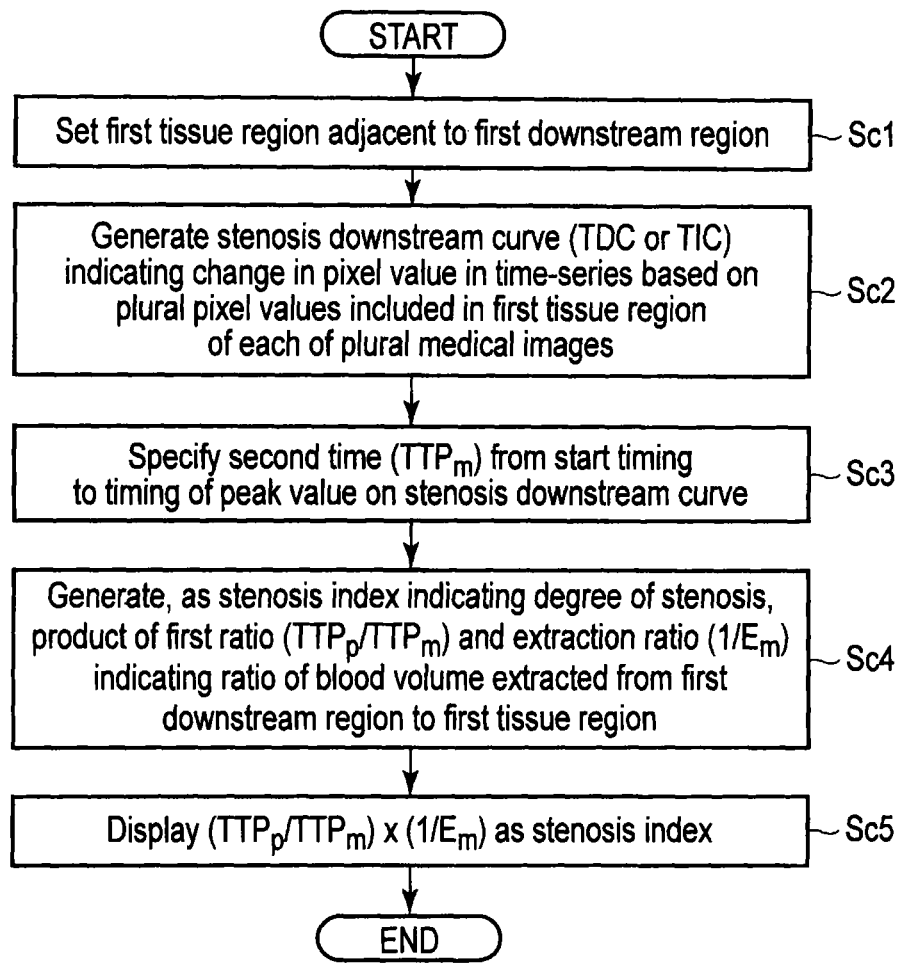
FIG. 19 is a flowchart illustrating an example of a procedure of generating a stenosis index according to the second modification of the embodiment.

In the second modification of this embodiment, a stenosis index may be generated as follows. FIG. 19 is a flowchart illustrating an example of a procedure of generating a stenosis index according to the second modification.

With a series of X-ray imaging operations on the subject, the image generating unit 24 generates a plurality of time-series medical images (angiographic images) of vasoganglion in a predetermined organ of the subject. The generated angiographic images are displayed on the display unit 23. In response to a command from the operator via the input unit 22, the region setting unit sets a first upstream region in the upstream portion of a stenosis location in a blood vessel on the displayed angiographic images. In response to a command from the operator via the input unit 22, the region setting unit sets a first tissue region adjacent to the first downstream region downstream of the stenosis location on the displayed angiographic images (step Sc1). The first tissue region is, for example, a myocardium.

Figure 9B:
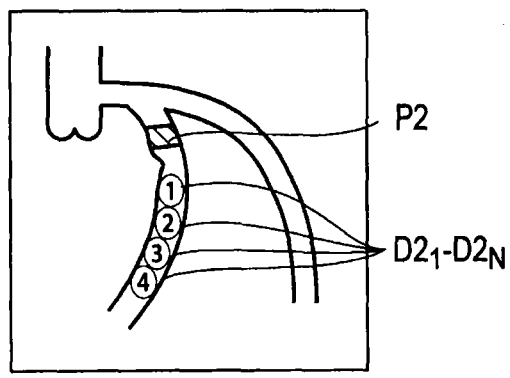
FIG. 9B is a diagram illustrating a second pair of exemplary locations for taking intensity measurements on the same branch of a blood vessel such as an artery according to the embodiment.
Figure 9C:
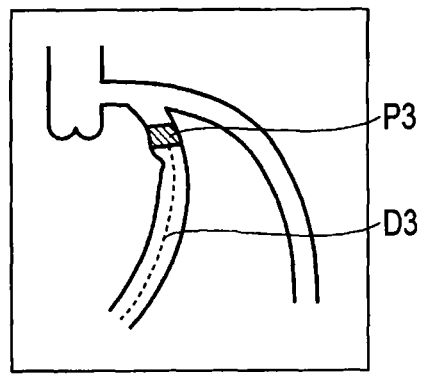
FIG. 9C is a diagram illustrating a third pair of exemplary locations for taking intensity measurements on the same branch of a blood vessel such as an artery according to the embodiment.
Figure 9D:
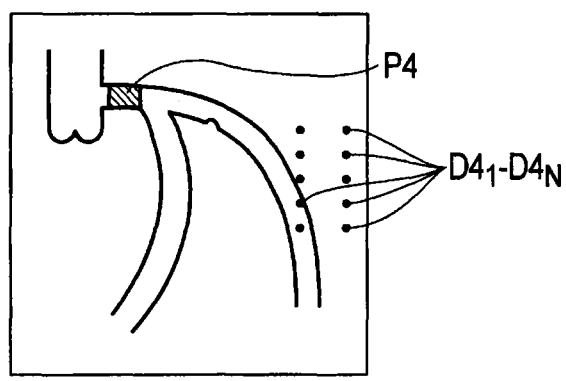
FIG. 9D is a diagram illustrating a fourth pair of exemplary locations for taking intensity measurements on the same branch of a blood vessel such as an artery according to the embodiment.
Figure 9E:
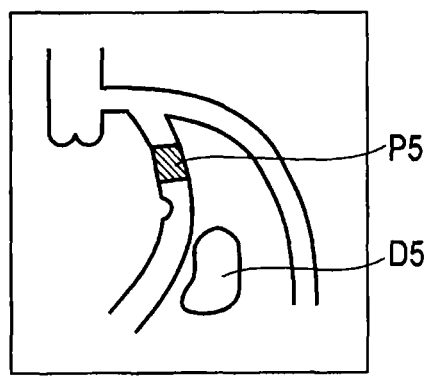
FIG. 9E is a diagram illustrating a fifth pair of exemplary locations for taking intensity measurements on the same branch of a blood vessel such as an artery according to the embodiment.

FIG. 9E is a diagram illustrating an example of the set first upstream region and the set first tissue region. In FIG. 9E, reference symbol P5 denotes a first upstream region; and D5, a first tissue region.

The curve generating unit 32 generates a stenosis upstream curve indicating a change in pixel value in a time-series based upon a plurality of pixel values included in the first upstream region of each of the plurality of medical images (angiographic images). The curve generating unit 32 also generates a stenosis downstream curve indicating a change in pixel value in a time-series based upon a plurality of pixel values included in the first tissue region of each of the plurality of medical images (angiographic images) (step Sc2).

The stenosis index generating unit 33 generates a stenosis index indicating the degree of stenosis in a stenotic vessel (first blood vessel) based upon the stenosis upstream curve and the stenosis downstream curve. More specifically, the stenosis index generating unit 33 specifies a first time ($TTP_p$) from the start timing of the stenosis upstream curve to the timing of its peak value (TTP (Time-To-Peak)) (step Sa5). The stenosis index generating unit 33 specifies a second time ($TTP_m$) from the start timing of the stenosis downstream curve to the timing of its peak value (TTP) (step Sc3).

Figure 20:
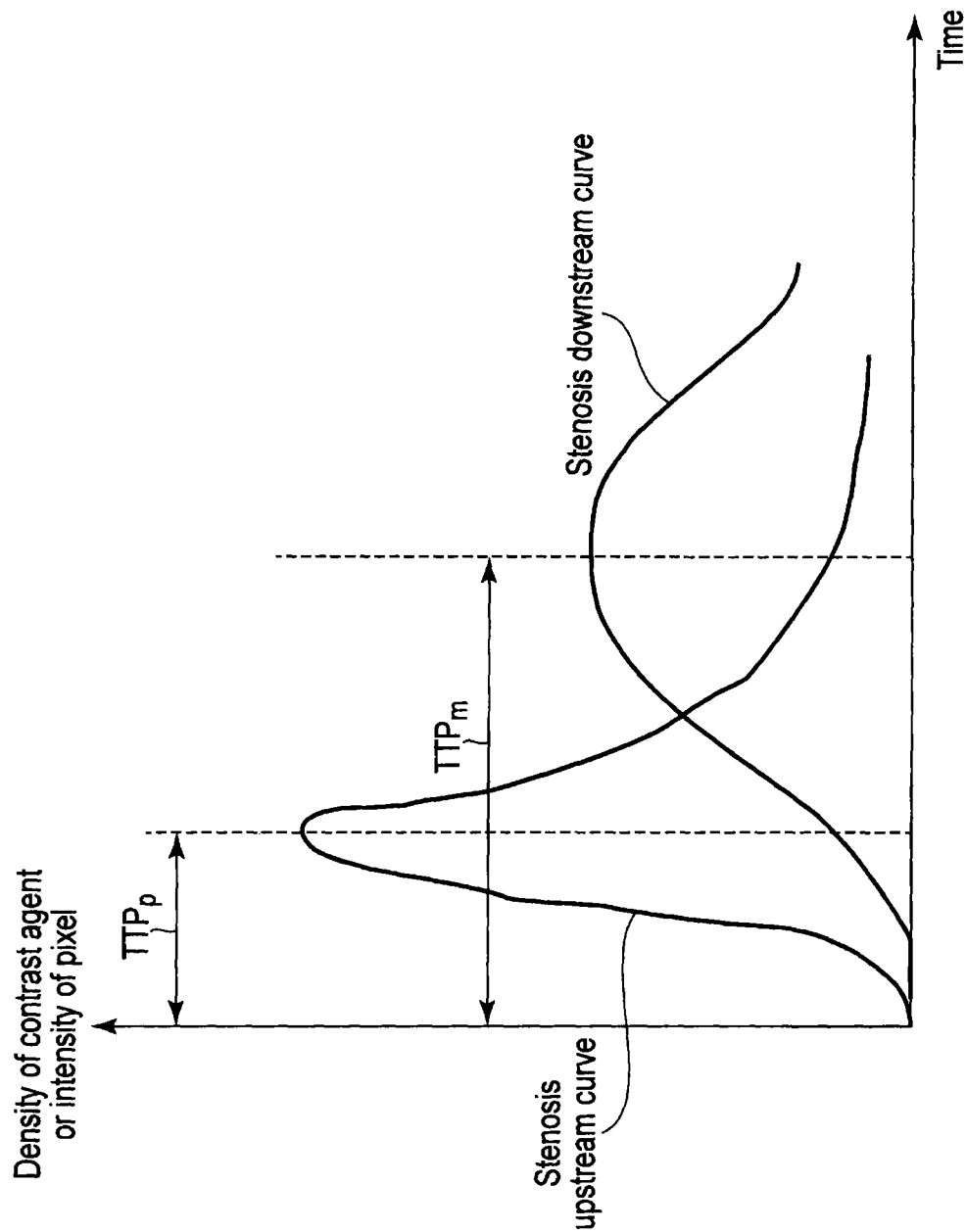
FIG. 20 is a timing chart illustrating a stenosis upstream curve and a stenosis downstream curve together with a first time ($TTP_p$) and a second time ($TTP_m$) according to the second modification of the embodiment.

FIG. 20 is a timing chart illustrating the stenosis upstream curve and the stenosis downstream curve together with the first time ($TTP_p$) and the second time ($TTP_m$). As shown in FIG. 20, the peak value of the TDC (TIC) in the first upstream region appears earlier than that of the TDC (TIC) in the first tissue region. Furthermore, the peak value of the TDC (TIC) in the first upstream region is larger than that of the TDC (TIC) in the first tissue region.

The stenosis index generating unit 33 determines a ratio (to be referred to as an extraction ratio ($1/E_m$) hereinafter) of a blood flow extracted from the first downstream region to the first tissue region based upon the stenosis downstream curve and the TDC or TIC in the first tissue region. Note that the image processing unit 26 may determine the extraction ratio $E_m$ in advance based upon the angiographic images. Furthermore, the extraction ratio may be stored in the storage unit 25 in advance.

The stenosis index generating unit 33 generates a stenosis index based upon the first time ($TTP_p$), second time ($TTP_m$), and extraction ratio ($1/E_m$). More specifically, the stenosis index generating unit 33 generates the product (($TTP_p$/$TTP_m$)×($1/E_m$)) of the first ratio ($TTP_p$/$TTP_m$) of the first time to the second time and the extraction ratio ($1/E_m$) as a stenosis index (step Sc4). The stenosis index generating unit 33 outputs the generated stenosis index to the display unit 23. The display unit 23 displays the stenosis index (($TTP_p$/($TTP_m \times E_m$))) generated by the stenosis index generating unit 33 (step Sc5).

Figure 21:
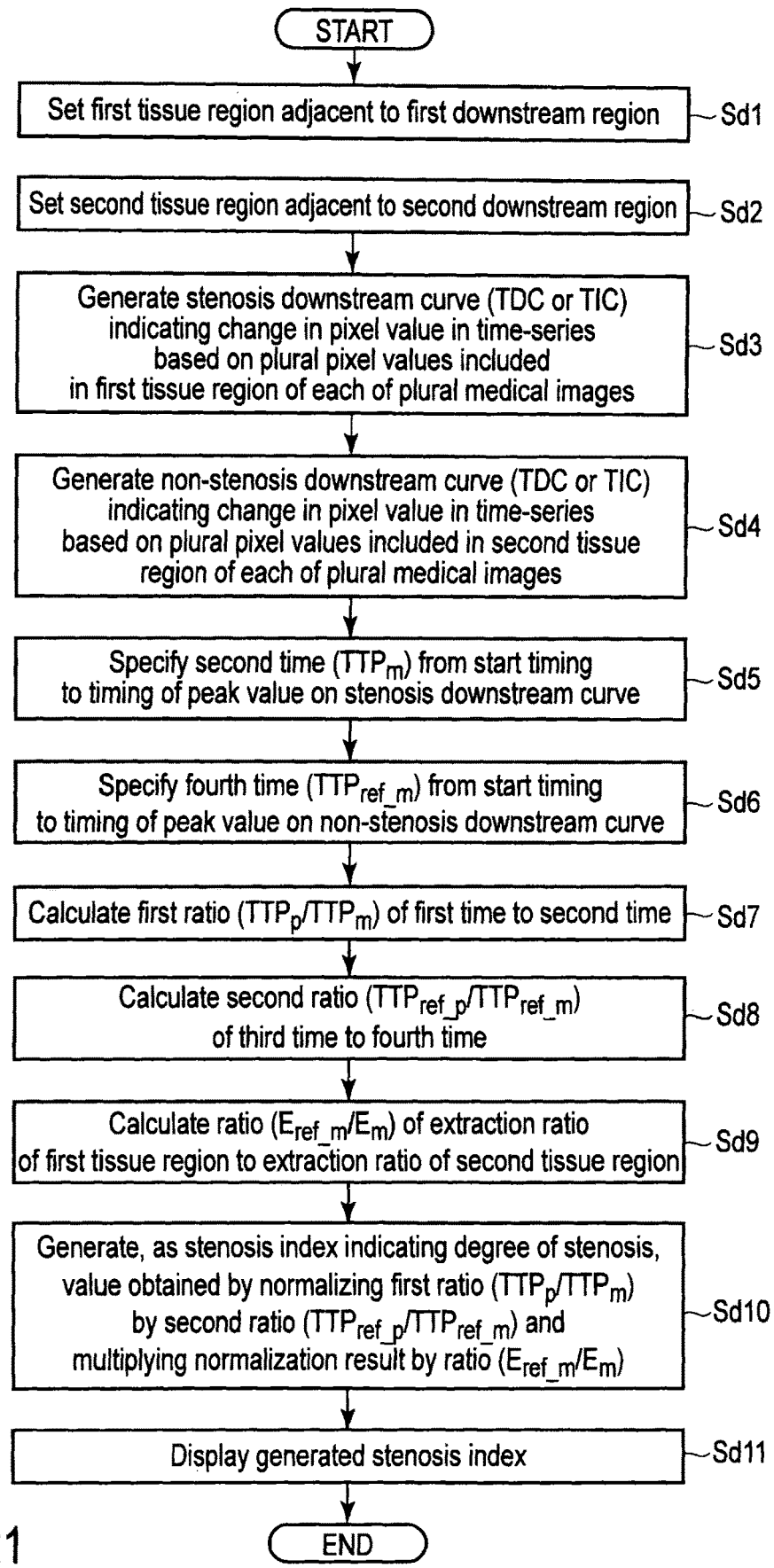
FIG. 21 is a flowchart illustrating an example of a procedure of generating a stenosis index according to the third modification of the embodiment.

In the third modification of this embodiment, a stenosis index may be generated as follows. FIG. 21 is a flowchart illustrating an example of a procedure of generating a stenosis index according to the third modification.

With a series of X-ray imaging operations on the subject, the image generating unit 24 generates a plurality of time-series medical images (angiographic images) of vasoganglion in a predetermined organ of the subject. The generated angiographic images are displayed on the display unit 23. In response to a command from the operator via the input unit 22, the region setting unit sets a first upstream region in the upstream portion of a stenosis location in the first blood vessel (stenotic vessel) on the displayed angiographic images. Furthermore, in response to a command from the operator via the input unit 22, the region setting unit sets a first tissue region adjacent to the first downstream region downstream of the stenosis location on the displayed angiographic images (step Sd1).

In response to a command from the operator via the input unit 22, the region setting unit sets a second tissue region adjacent to the second downstream region on the displayed angiographic images (step Sd2). More specifically, the second downstream region is set in a non-stenotic vessel so that the distance from a branching portion to the first downstream region becomes equal to that from the branching portion to the second downstream region. The first tissue region or the second tissue region is, for example, a myocardium positioned downstream of the stenosis location.

Figure 5C:
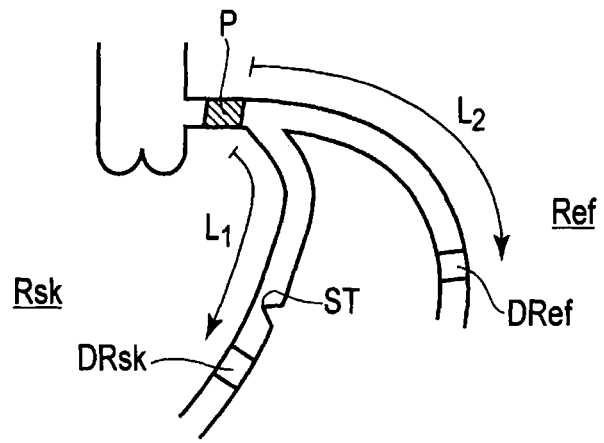
FIG. 5C is a diagram illustrating exemplary measurement locations for determining time-density data from the angiographic image data as acquired in a region of interest that includes a predetermined risk artery and a predetermined reference artery that share a common location according to the embodiment.
Figure 5D:
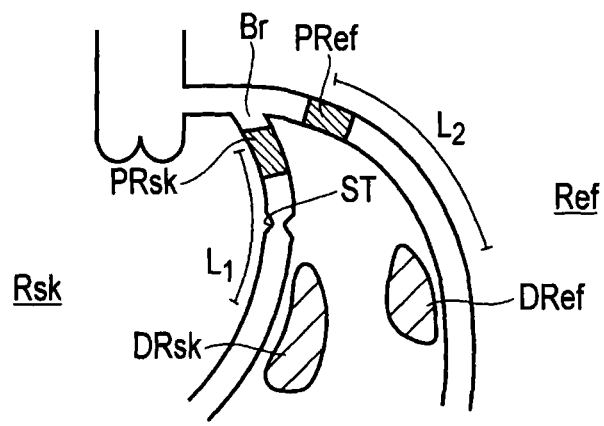
FIG. 5D is a diagram illustrating exemplary measurement locations for determining time-density data from the angiographic image data as acquired in a region of interest that includes a predetermined risk artery, a predetermined reference artery, and regions outside of these arteries according to the embodiment.

FIG. 5D is a diagram illustrating a first upstream region and a first tissue region which are set in a stenotic vessel, and a second upstream region and a second tissue region which are set in a non-stenotic vessel (second blood vessel). Referring to FIG. 5D, reference symbol PRsk denotes a first upstream region; DRsk, a first tissue region; ST, a stenosis location in the stenotic vessel; PRef, a second upstream region; and DRef, a second tissue region. As shown in FIG. 5D, a distance L1 between the first upstream region and the first tissue region is equal to a distance L2 between the second upstream region and the second tissue region.

The curve generating unit 32 generates a stenosis downstream curve indicating a change in pixel value in a time-series based upon a plurality of pixel values included in the first tissue region of each of the plurality of medical images (angiographic images) (step Sd3). The curve generating unit 32 also generates a non-stenosis downstream curve indicating a change in pixel value in a time-series based upon a plurality of pixel values included in the second tissue region of each of the plurality of medical images (angiographic images) (step Sd4). The stenosis downstream curve and the non-stenosis downstream curve are curves (TDCs (Time-Density Curves) or TICs (Time-Intensity Curves)) each indicating a change in pixel value, that is, density of the contrast agent (or intensity of a pixel value) with time.

The stenosis index generating unit 33 generates a stenosis index indicating the degree of stenosis in the first blood vessel (stenotic vessel) based upon the stenosis upstream curve, stenosis downstream curve, non-stenosis upstream curve, and non-stenosis downstream curve. More specifically, the stenosis index generating unit 33 specifies a second time ($TTP_m$) from the start timing of the stenosis downstream curve to the timing of its peak value (TTP (Time-To-Peak)) (step Sd5). The stenosis index generating unit 33 specifies a fourth time ($TTP_{ref\_m}$) from the start timing of the non-stenosis downstream curve to the timing of its peak value (TTP) (step Sd6).

Figure 22:
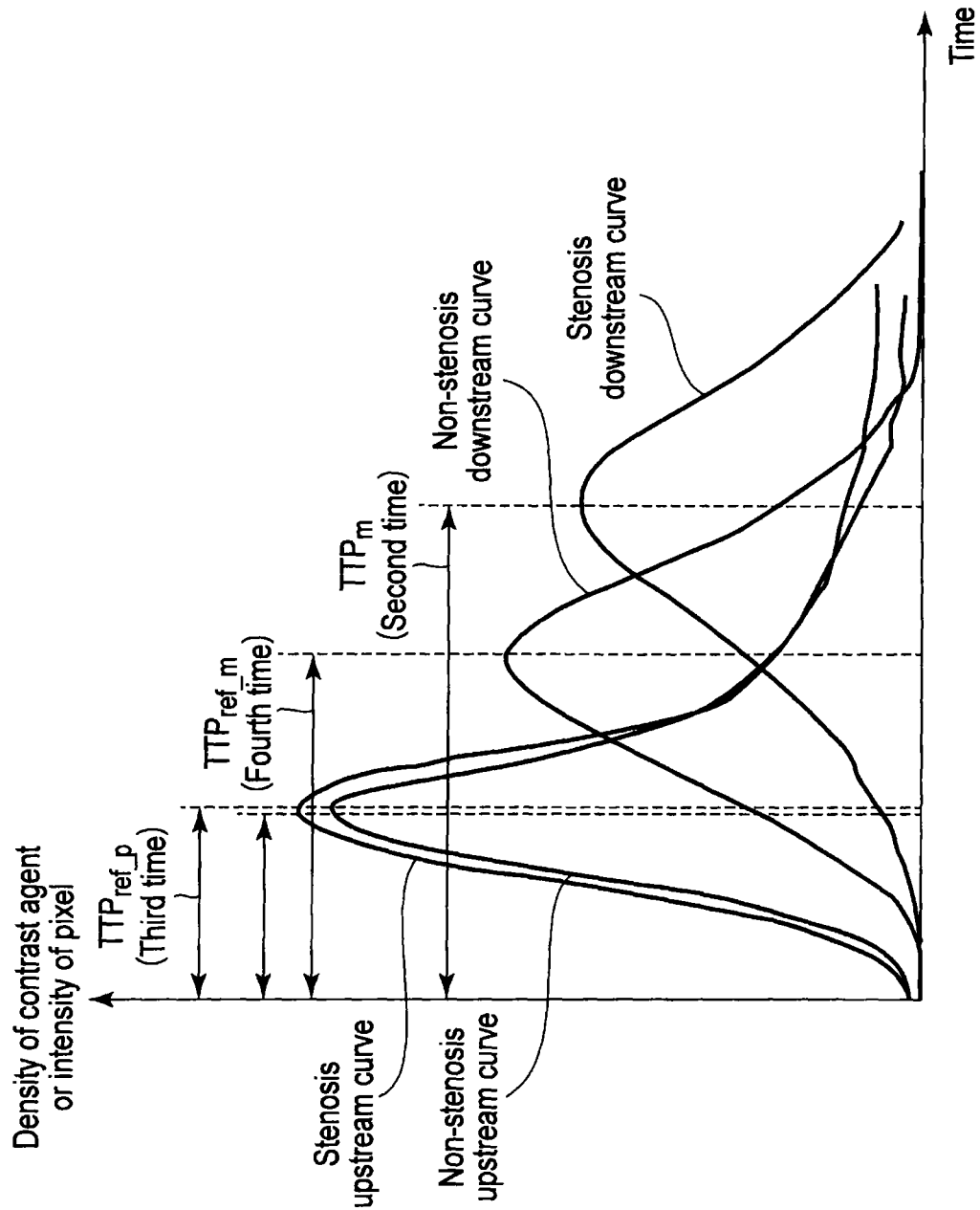
FIG. 22 is a timing chart illustrating a stenosis upstream curve, a stenosis downstream curve, a non-stenosis upstream curve, and a non-stenosis downstream curve together with a first time ($TTP_p$), a second time ($TTP_m$), a third time ($TTP_{ref\_p}$), and a fourth time ($TTP_{ref\_m}$) according to the third modification of the embodiment.

FIG. 22 is a timing chart illustrating the stenosis upstream curve, stenosis downstream curve, non-stenosis upstream curve, and non-stenosis downstream curve together with the first time ($TTP_p$), second time ($TTP_m$), third time ($TTP_{ref\_p}$), and fourth time ($TTP_{ref\_m}$). As shown in FIG. 22, the peak value of the stenosis downstream curve (TDC (TIC) in the first downstream region) appears later than that of the non-stenosis downstream curve (TDC (TIC) in the second downstream region) due to stenosis in the blood vessel.

The stenosis index generating unit 33 calculates the first ratio between the first time and the second time. The stenosis index generating unit 33 also calculates the second ratio between the third time and the fourth time. More specifically, the stenosis index generating unit 33 calculates the ratio ($TTP_p$/$TTP_m$) of the first time to the second time as the first ratio (step Sd7). The stenosis index generating unit 33 calculates the second ratio ($TTP_{ref\_p}$/$TTP_{ref\_m}$) of the third time to the fourth time (step Sd8).

The stenosis index generating unit 33 determines a ratio (to be referred to as a first extraction ratio ($1/E_m$) hereinafter) of a blood flow extracted from the first downstream region to the first tissue region based upon the stenosis downstream curve and the TDC or TIC in the first tissue region. The stenosis index generating unit 33 determines a ratio (to be referred to as a second extraction ratio ($1/E_{ref\_m}$) hereinafter) of a blood flow extracted from the second downstream region to the second tissue region based upon the non-stenosis downstream curve and the TDC or TIC in the second tissue region.

The stenosis index generating unit 33 calculates the ratio ($E_{ref\_m}/E_m$) of the first extraction ratio ($1/E_m$) to the second extraction ratio ($1/E_{ref\_m}$) (step Sd9). Note that the image processing unit 26 may determine the first extraction ratio $E_m$ and the second extraction ratio $E_{ref\_m}$ in advance based upon the angiographic images. Furthermore, the first extraction ratio and the second extraction ratio may be stored in the storage unit 25 in advance.

The stenosis index generating unit 33 generates a stenosis index based upon the first time ($TTP_p$), second time ($TTP_m$), third time ($TTP_{ref\_p}$), fourth time ($TTP_{ref\_m}$) first extraction ratio ($1/E_m$), and second extraction ratio ($1/E_{ref\_m}$). More specifically, the stenosis index generating unit 33 generates, as a stenosis index in the stenotic vessel (first blood vessel), the product of the ratio ($E_{ref\_m}/E_m$) and a value (($TTP_p$/$TTP_m$)/($TTP_{ref\_p}$/$TTP_{ref\_m}$)) obtained by normalizing the first ratio by the second ratio (step Sd10).

The stenosis index generating unit 33 outputs the generated stenosis index to the display unit 23. The display unit 23 displays ($TTP_p \times TTP_{ref\_m} \times E_{ref\_m}$)/($TTP_m \times TTP_{ref\_p} \times E_m$) as an stenosis index (step Sd11).

By summarizing the definition of a stenosis index in the second modification and this embodiment, for example, a diagram shown in FIG. 9G is obtained. The first upstream region in the embodiment and the second modification corresponds to a region P7 shown in FIG. 9G. The first downstream region in the embodiment corresponds to a region $D7_1$ shown in FIG. 9G. The first tissue region in the second modification corresponds to a region $D7_2$ shown in FIG. 9G.

TDCs or TICS corresponding to the three regions P7, $D7_1$, and $D7_2$ shown in FIG. 9G are as illustrated in FIGS. 23 and 24. Each of FIGS. 23 and 24 is a timing chart illustrating a plurality of TDCs (or a plurality of TICs) corresponding to the first upstream region, the first downstream region in the stenotic vessel, and the first tissue region.

As shown in FIG. 23, $TTP_p$ (first time) used in the embodiment and the second modification is specified as the time from the start timing of the stenosis upstream curve to the timing of its peak value. As shown in FIG. 23, $TTP_d$ (second time) used in the embodiment is specified as the time from the start timing of the stenosis upstream curve to the timing of the peak value of the stenosis downstream curve. As shown in FIG. 23, $TTP_m$ (second time) used in the second modification is specified as the time from the start time of the stenosis upstream curve to the timing of the peak value of the stenosis downstream curve.

As shown in FIG. 24, TTP (first time) used in the embodiment and the second modification is specified as the time from the start timing of the stenosis upstream curve to the timing of its peak value. As shown in FIG. 24, $TTP_d$ (second time) used in the embodiment is specified as the time from the start time of the stenosis downstream curve to the timing of its peak value. As shown in FIG. 24, $TTP_m$ (second time) used in the second modification is specified as the time from the start time of the stenosis downstream curve to the timing of its peak value.

In accordance with TTP (first time), $TTP_d$ (second time), and $TTP_m$ (second time) shown in FIGS. 23 and 24, three stenosis indexes (to be described below) respectively corresponding to three different FFRs can be defined. A stenosis index (a stenosis index calculated in the embodiment) corresponding to the FFR of the stenotic vessel is ($TTP_p$ (first time)/$TTP_d$ (second time)). A stenosis index (a stenosis index different from that in the embodiment and the first to third modifications) corresponding to the microvascular FFR of the stenotic vessel is ($TTP_d$ (second time)/$TTP_m$ (second time)). A stenosis index (a stenosis index calculated in the second modification) corresponding to the FFR of the tissue region is ($TTP_d$ (second time)/$TTP_m$ (second time)).

Note that the stenosis index calculated in the embodiment and the first to third modifications has been explained by exemplifying a coronary artery in a heart region. However, a stenosis index may be calculated for a blood vessel of another organ. The other organ is, for example, a brain. In this case, a stenosis index is generated for a blood vessel in the brain.

Figure 25:
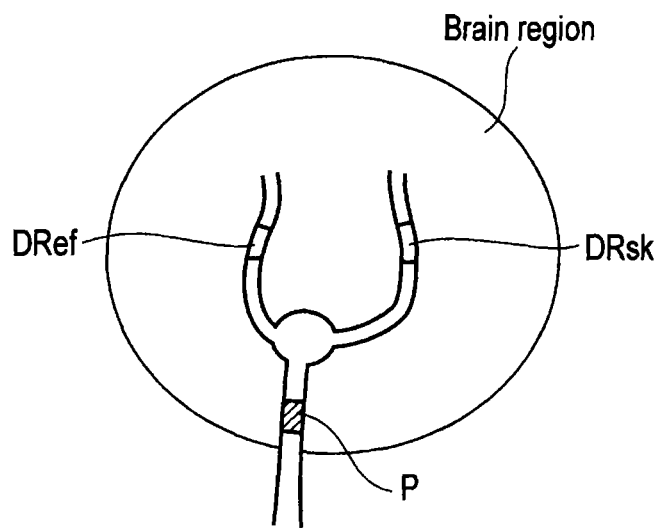
FIG. 25 is a diagram illustrating an example of regions set for generating stenosis indexes by setting blood vessels in a brain region as targets according to the embodiment.
Figure 26:
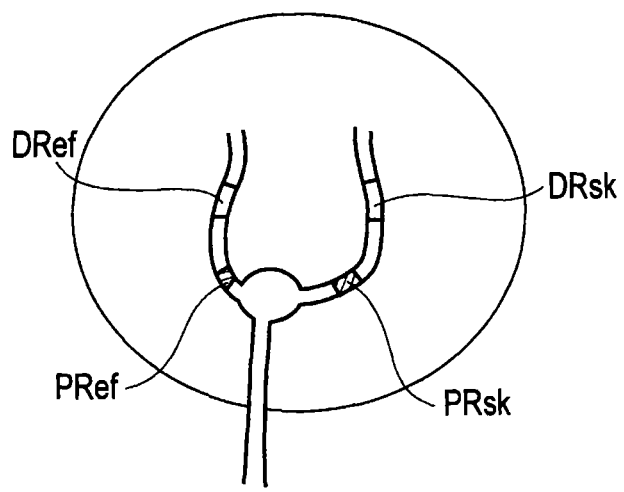
FIG. 26 is a diagram illustrating an example of regions set for generating stenosis indexes by setting blood vessels in a brain region as targets according to the embodiment.

Each of FIGS. 25 and 26 is a diagram illustrating an example of a region set to generate a stenosis index for a blood vessel in the brain region. A region P shown in FIG. 25 corresponds to the first upstream region and the second upstream region. A region DRsk shown in FIG. 25 corresponds to the first downstream region. A region DRef shown in FIG. 25 corresponds to the second downstream region. A region PRsk shown in FIG. 26 corresponds to the first upstream region. A region PRef shown in FIG. 26 corresponds to the second upstream region. A region DRsk shown in FIG. 26 corresponds to the first downstream region. A region DRef shown in FIG. 26 corresponds to the second downstream region.

Note that the stenosis index generating unit 33 may generate stenosis indexes for the whole region of the angiographic image based upon, for example, the first time in the first upstream region and the TTPs of all the pixels of the angiographic image. More specifically, the stenosis index generating unit 33 calculates stenosis indexes for all the pixels of the angiographic image from their TTPs with reference to the first time in the first upstream region. Note that the stenosis index generating unit 33 may calculate stenosis indexes for some pixels. FIG. 9D is a diagram illustrating an example of points of some pixels for which stenosis indexes are calculated.

In this case, the stenosis index generating unit 33 outputs the stenosis indexes for all the pixels to the display unit 23. The display unit 23 superimposes and displays the stenosis indexes for all the pixels on the angiographic image on a gray scale (or color scale). Note that if stenosis indexes are calculated for some pixels, the display unit 23 displays the stenosis indexes for some pixels. FIG. 10C is a diagram illustrating a case in which stenosis indexes for some pixels of the angiographic image are superimposed and displayed.

Note that in this embodiment, a plurality of time-series medical images to be processed may be generated by imaging the subject from a plurality of projection directions. At this time, a plurality of stenosis indexes respectively corresponding to the projection directions are generated. For example, the stenosis index generating unit 33 integrates the plurality of stenosis indexes. The integrated stenosis indexes are displayed on the display unit 23. Note that the stenosis index generating unit 33 may normalize the plurality of stenosis indexes with reference to a stenosis index corresponding to one of the plurality of projection directions. At this time, the stenosis indexes normalized by the one projection direction are displayed on the display unit 23.

Now referring to FIG. 2, FIG. 2 illustrates one X-ray CT apparatus or scanner including a gantry 100 and other devices or units. The gantry 100 is illustrated from a side view and further includes an X-ray tube 101, an annular frame 102, and a multi-row or two-dimensional array type X-ray detector 103. The X-ray 101 and X-ray detector 103 are diametrically mounted across a subject S on the annular frame 102, which is rotatably supported around a rotation axis RA. A rotating unit 107 rotates the annular frame 102 at a high speed such as 0.4 sec/rotation while the subject S is being moved along the axis RA into or out of the illustrated page.

The multi-slice X-ray CT apparatus further includes a high-voltage generator 109 and a tube current adjusting unit 111 that respectively control a tube voltage and a tube current in the X-ray tube 101 through a slip ring 108 so that the X-ray tube 101 generates X-rays in response to a system controlling unit 110. The X-rays are emitted towards the subject S, whose cross-sectional area is represented by a circle. The X-ray detector 103 is located on the opposite side of the X-ray tube 101 across the subject S for detecting the emitted X-rays that have been transmitted through the subject S. The X-ray detector 103 further includes individual detector elements or units that are conventional integrating detectors.

Still referring to FIG. 2, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to process a predetermined total number of projections per rotation (TPPR). The TPPR is at the most 900 TPPR, between 900 TPPR and 1800 TPPR and between 900 TPPR and 3600 TPPR.

The above-described data is sent to a preprocessing unit 106, which is housed in a console outside the gantry 100, through a noncontact data transmitting unit 105. The preprocessing unit 106 performs certain correction such as sensitivity correction on raw data. A storage unit 112 then stores the resultant data that is also called projection data at a stage immediately before reconstruction processing. The storage unit 112 is connected to the system controlling unit 110 through a data/control bus, together with a reconstructing unit 114, an input unit 115, a display unit 116, a blood circulation determining unit (stenosis index generating unit) 117, a treatment determining unit 118, and a scan plan support apparatus 200. The scan plan support apparatus 200 includes a function for supporting an imaging technician to develop a scan plan.

In this embodiment, equipment related to blood circulation is required to perform the injection of a predetermined contrast agent into the subject S. For example, a predetermined contrast agent is injected in bolus into the left ventricular cavity in a coronary study prior to scanning. A circulation technique is not going to be described in details here, but well-known circulation techniques are generally applicable to the current invention.

One embodiment of the blood circulation determining unit 117 further includes a combination of various software and hardware components. According to one aspect of this embodiment, the blood circulation determining unit 117 of the CT apparatus advantageously determines a predetermined time-based fractional flow reserve (FFR) based upon the angiographic image data that is acquired by the X-ray CT apparatus. In general, the blood circulation determining unit 117 in this embodiment initially generates time-density data such as time-density curves (TDCs) at predetermined locations along a selected blood vessel from the angiographic image data. The predetermined locations generally include at least a proximal location and a distal location. The proximal location is proximal to (upstream of) a suspected stenosis location in the selected blood vessel and is substantially free from any blockage for blood circulation. On the other hand, the distal location is distal to (downstream of) the suspected stenosis location in the selected blood vessel and is potentially affected by the blockage for blood circulation. Ultimately, the blood circulation determining unit 117 determines a predetermined time-based index (stenosis index) such as a time-based FFR for evaluating a level of blood circulation between two locations such as the proximal location and the distal location in a selected blood vessel in the region of interest. Thus, both of two data points are used to determine a time-based FFR (stenosis index) in the first embodiment of the blood circulation determining unit 117 according to this embodiment.

In the second embodiment of the blood circulation determining unit 117 further includes a combination of various software and hardware components. According to one aspect of this embodiment, the blood circulation determining unit 117 of the X-ray CT apparatus advantageously determines a predetermined time-based fractional flow reserve (FFR) (stenosis index) based upon the angiographic image data that is acquired by the X-ray CT apparatus. In general, the blood circulation determining unit 117 in the second embodiment initially generates time-density data such as time-density curves (TDCs) at predetermined locations along a pair of selected blood vessels from the angiographic image data. The pair of selected blood vessels generally includes a predetermined risk blood vessel (first blood vessel) and a predetermined reference blood vessel (second blood vessel). The predetermined risk blood vessel is a blood vessel under investigation for suspected stenosis that contributes to some blockage in blood circulation. On the other hand, the predetermined reference blood vessel is a blood vessel separate from the predetermined risk blood vessel and is used as a reference to assure the evaluation for suspected stenosis in the predetermined risk blood vessel. In general, the predetermined reference blood vessel is selected from a group of healthy blood vessels that is comparable in size and location to the predetermined risk blood vessel and is substantially away from stenosis.

In the second embodiment, the blood circulation determining unit 117 also generates time-density data such as time-density curves (TDCs) at predetermined locations along each pair of blood vessels selected from the angiographic image data. The predetermined locations generally include at least a proximal location and a distal location along each of the two selected blood vessels. In the predetermined risk blood vessel, the proximal location is proximal to (upstream of) a suspected stenosis location and is substantially free from any blockage for blood circulation. On the other hand, the distal location (downstream) in the predetermined risk blood vessel is distal to the suspected stenosis location and is potentially affected by the blockage for blood circulation. In the predetermined reference blood vessel, the proximal and distal locations are locations that are respectively comparable to the proximal location and the distal location of the predetermined risk blood vessel. Ultimately, the blood circulation determining unit 117 determines a predetermined time-based index (stenosis index) such as a time-based FFR for evaluating a level of blood circulation between two locations such as the proximal location and the distal location in a selected blood vessel in the region of interest. Thus, all of four data points are used to determine a time-based FFR in the second embodiment of the blood circulation determining unit 117.

One embodiment of the treatment determining unit 118 further includes various software and hardware components. According to one aspect of this embodiment, the treatment determining unit 118 of the X-ray CT apparatus advantageously determines whether or not a certain medical procedure should be performed on the patient based upon a blockage index (stenosis index) that the blood circulation determining unit 117 has output for a particular blood vessel. For example, if the blood circulation determining unit 117 has output a particular FFR value (stenosis index), the treatment determining unit 118 advantageously determines whether or not a stent should be inserted into the measured coronary artery based upon the FFR value (stenosis index) and outputs a proposed medical decision. The treatment determining unit 118 optionally displays the relevant information including the proposed medical decision via the display unit 116.

As will be further described below, the embodiment is not limited to the specific features of the above disclosures. The blood circulation determining unit 117 according to this embodiment is not limited to certain aspects of the time-density data (time-density curve) to determine a predetermined fractional flow reserve (FFR) (stenosis index). For example, one embodiment of the blood circulation determining unit 117 utilizes the time-to-peak (TTP) information, mean-transit-time (MTT) information, and/or upward slope information of the time-density curves (TDCs), and another embodiment optionally uses different aspects of the time-density data (time-density curve) that has been generated from the angiographic image data with respect to the blood vessels and the surrounding tissues. Similarly, the treatment determining unit 118 optionally considers other factors or information in addition to the output index (stenosis index) from the blood circulation determining unit 117.

Similarly, the embodiment is not limited to the specific features of the above-disclosed embodiments of the X-ray CT apparatus. In other words, the embodiment is applicable to other modalities including an ultrasound diagnostic apparatus, various computed tomography (CT) apparatuses, a magnetic resonance imaging (MRI) apparatus, and an angiography and positron emission tomography (PET) apparatus. In fact, the embodiment is implemented on a C-arm X-ray system (X-ray diagnostic apparatus) in angiography. In this regard, the time-density data such as time-density curves (TDCs) is generated from certain imaging data including but not limited to angiographic image data and angiographic imaging data.

Figure 3:
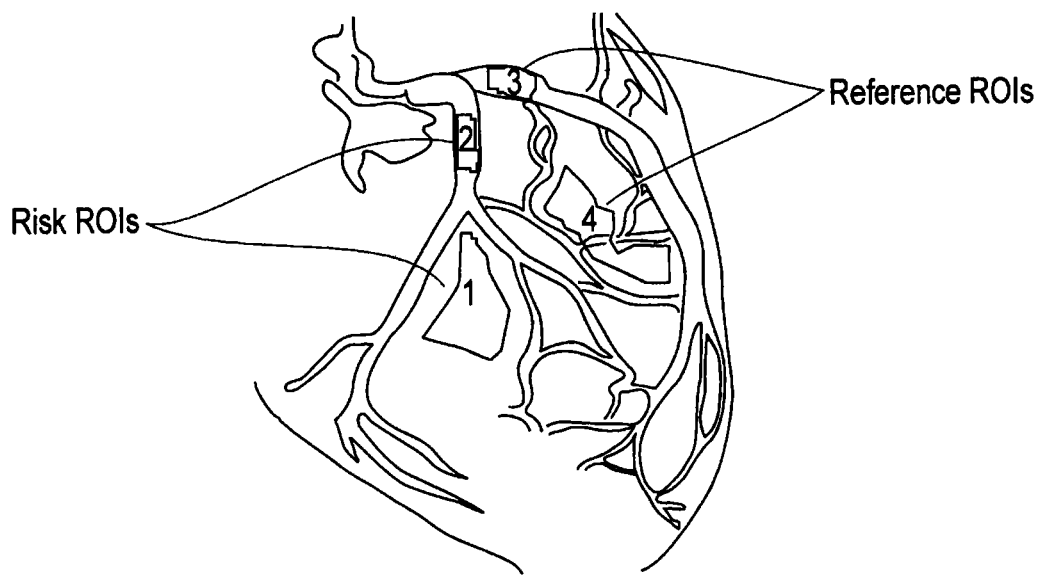
FIG. 3 is a diagram illustrating an exemplary image data set with a fixed view angle for optimally visualizing a risk coronary artery to be used as data according to the embodiment.

Now referring to FIG. 3, one exemplary image data set has a fixed view angle for optimally visualizing a risk coronary artery according to the embodiment. The exemplary X-ray image is a 2-dimensional image. Because of an optimal projection view angle (projection direction), one data acquisition protocol is to measure all the data points from the same single image set. The exemplary X-ray image shows on the left hand side a predetermined risk blood vessel and a predetermined risk region of interest (ROI). Similarly, the same exemplary X-ray image shows on the right hand side the predetermined reference blood vessel and a predetermined reference region of interest (ROI) that are comparable in size and location to the predetermined risk blood vessel and the predetermined risk region of interest (ROI) as shown on the left hand side. A plurality of density measurements are taken from the single image, and other density measurements are also made from comparable single images that have been scanned at the optimal projection view angle (projection direction) over time. Based upon these measurements, time-density data is generated as risk time-density curves (TDCs) and reference time-density curves (TDCs) from one set of images according to a first data acquisition protocol of this embodiment.

Figure 4A:
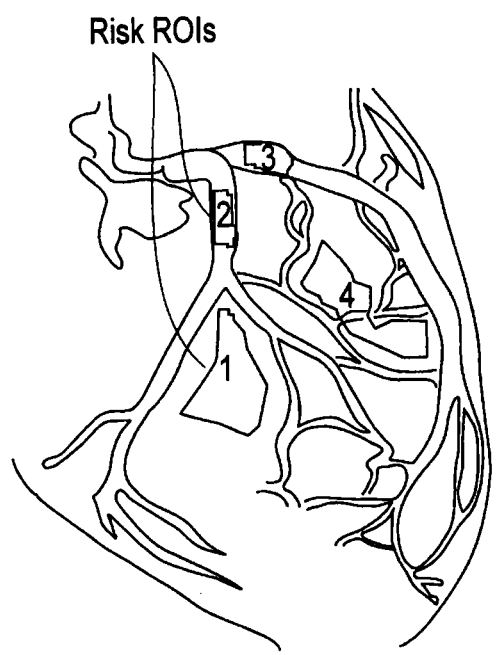
FIG. 4A is a diagram illustrating a set of exemplary images respectively having different fixed view angles for optimally visualizing a certain coronary artery to be used as data according to the embodiment.
Figure 4B:
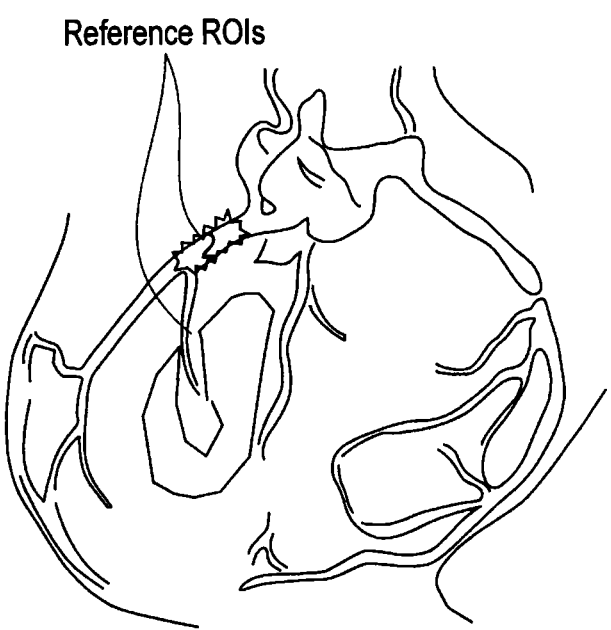
FIG. 4B is a diagram illustrating a set of exemplary images respectively having different fixed view angles for optimally visualizing a certain coronary artery to be used as data according to the embodiment.

Now referring to FIGS. 4A and 4B, two sets of exemplary images respectively have different fixed view angles for optimally visualizing a certain coronary artery according to this embodiment. The exemplary X-ray images are 2-dimensional images, and each of the two image data sets has an optimal view angle. That is, the data sets of FIGS. 4A and 4B respectively have different optimal projection view angles to a risk coronary artery and a reference coronary artery. Because of the different optimal projection view angles, a second data acquisition protocol is to measure some data points from one image set and other data points from the other image set. The exemplary X-ray image as illustrated in FIG. 4A shows on the left hand side a predetermined risk blood vessel and a predetermined risk region of interest (ROI).

Similarly, the exemplary X-ray image as illustrated in FIG. 4B shows also on the left hand side a predetermined reference blood vessel and a predetermined reference region of interest (ROI) that are comparable in size and location to the predetermined risk blood vessel and the predetermined risk region of interest (ROI) as shown on the left hand side of FIG. 4A. A plurality of density measurements are taken from the two image sets, and other density measurements are also made from comparable image data sets that have been scanned at the different optimal projection view angles over time. Based upon these measurements, time-density data is generated as risk time-density curves (TDCs) and reference time-density curves (TDCs) from the two sets of images according to the second data acquisition protocol of this embodiment.

Now referring to FIG. 5A, a diagram illustrates exemplary measurement locations for determining time-density data from the angiographic image data as acquired in a region of interest that includes a predetermined risk artery and a predetermined reference artery according to this embodiment. In this example and other examples, the term "artery" is synonymously used with a blood vessel, and blood vessels generally include arteries and veins as well as capillaries. On the left side, a predetermined risk artery Rsk is shown with stenosis ST that restricts a blood flow due to its blocking effect. Across the stenosis ST, a risk artery proximal location PRsk is located closer to an artery branching point Br where blood flows towards the risk artery proximal location PRsk along the predetermined risk artery Rsk. On the other hand, a risk artery distal location DRsk is located farther away from the artery branching point Br across the stenosis ST along the predetermined risk artery Rsk.

Still referring to FIG. 5A, on the right side, a predetermined reference artery Ref is shown to be substantially free from any stenosis and to be comparable in size and location to the predetermined risk artery Rsk. Since the thicknesses of the two arteries Ref and Rsk are substantially equal over the equal distances $L_1$ and $L_2$, the predetermined reference artery Ref is comparable to the predetermined risk artery Rsk in size. Furthermore, because of the symmetrical configuration across the artery branching point Br, the predetermined reference artery Ref is also comparable to the predetermined risk artery Rsk in location. In this regard, a reference artery proximal location PRef is located along the predetermined reference artery Ref and as comparably close to the artery branching point Br as the risk artery proximal location PRsk. On the other hand, a reference artery distal location DRef is located along the predetermined reference artery Ref and as comparably far away from the artery branching point Br as the risk artery distal location DRsk. In this embodiment, all of four data points are determined at the risk artery proximal location PRsk, the risk artery distal location DRsk, the reference artery proximal location PRef, and the reference artery distal location DRef for generating time-density data according to this embodiment.

Now referring to FIG. 5B, a diagram illustrates exemplary measurement locations for determining time-density data from the angiographic image data as acquired in a region of interest that includes a predetermined risk artery and a predetermined reference artery according to this embodiment. On the left side, a predetermined risk artery Rsk is shown with stenosis ST that restricts a blood flow due to its blocking effect. Across the stenosis ST, a risk artery proximal location PRsk is located closer to an artery branching point Br where blood flows towards the risk artery proximal location PRsk along the predetermined risk artery Rsk. On the other hand, a risk artery distal location DRsk is located farther away from the artery branching point Br across the stenosis ST along the predetermined risk artery Rsk.

Still referring to FIG. 5B, on the right side, a predetermined reference artery Ref is shown to be substantially free from any stenosis and to be comparable in size and location to the predetermined risk artery Rsk. Since the thicknesses of the two arteries Ref and Rsk are substantially equal over the equal distances $L_1$ and $L_2$, the predetermined reference artery Ref is comparable to the predetermined risk artery Rsk in size. Despite the asymmetrical configuration across the artery branching point Br, the predetermined reference artery Ref is still assumed to be comparable to the predetermined risk artery Rsk in location due to their vicinity with each other and the common branching point Br. In this regard, a reference artery proximal location PRef is located along the predetermined reference artery Ref and as comparably close to the artery branching point Br as the risk artery proximal location PRsk. On the other hand, a reference artery distal location DRef is located along the predetermined reference artery Ref and as comparably far away from the artery branching point Br as the risk artery distal location DRsk. In this embodiment, all of four data points are determined at the risk artery proximal location PRsk, the risk artery distal location DRsk, the reference artery proximal location PRef, and the reference artery distal location DRef for generating time-density data according to this embodiment.

Now referring to FIG. 5C, a diagram illustrates exemplary measurement locations for determining time-density data from the angiographic image data as acquired in a region of interest that includes a predetermined risk artery and a predetermined reference artery according to this embodiment. On the left side, a predetermined risk artery Rsk is shown with stenosis ST that restricts a blood flow due to its blocking effect. Across the stenosis ST, a common proximal location P is located upstream and near an artery branching point Br where the predetermined risk artery Rsk and the predetermined reference artery Ref branch. On the other hand, a risk artery distal location DRsk is located farther away from the artery branching point Br across the stenosis ST along the predetermined risk artery Rsk.

Still referring to FIG. 5C, on the right side, the predetermined reference artery Ref is shown to be substantially free from any stenosis and to be comparable in size and location to the predetermined risk artery Rsk. Since the thicknesses of the two arteries Ref and Rsk are substantially equal over the equal distances $L_1$ and $L_2$, the predetermined reference artery Ref is comparable to the predetermined risk artery Rsk in size. Because of the substantially symmetrical configuration across the artery branching point Br, the predetermined reference artery Ref is assumed to be comparable to the predetermined risk artery Rsk in location due to their vicinity with each other and the common branching point Br. In this regard, the common proximal location is shared between the predetermined reference artery Ref and the predetermined risk artery Rsk. On the other hand, a reference artery distal location DRef is located along the predetermined reference artery Ref and as comparably far away from the artery branching point Br as the risk artery distal location DRsk. In this embodiment, all of three data points are determined at the common proximal location P, the risk artery distal location DRsk, and the reference artery distal location DRef for generating time-density data according to this embodiment.

Now referring to FIG. 5D, a diagram illustrates exemplary measurement locations for determining time-density data from the angiographic image data as acquired in a region of interest that includes a predetermined risk artery and a predetermined reference artery according to this embodiment. In this example and other examples, the term "artery" is synonymously used with a blood vessel, and blood vessels generally include arteries and veins as well as capillaries. On the left side, a predetermined risk artery Rsk is shown with stenosis ST that restricts a blood flow due to its blocking effect. Across the stenosis ST, a risk artery proximal location PRsk is located closer to an artery branching point Br where blood flows towards the risk artery proximal location PRsk along the predetermined risk artery Rsk. On the other hand, a risk artery distal location DRsk is located farther away from the artery branching point Br across the stenosis ST along the predetermined risk artery Rsk.

Still referring to FIG. 5D, on the right side, a predetermined reference artery Ref is shown to be substantially free from any stenosis and to be comparable in size and location to the predetermined risk artery Rsk. Since the diameters of the two arteries Ref and Rsk are substantially equal over the equal distances $L_1$ and $L_2$, the predetermined reference artery Ref is comparable to the predetermined risk artery Rsk in size. Furthermore, because of the symmetrical configuration across the artery branching point Br, the predetermined reference artery Ref is also comparable to the predetermined risk artery Rsk in location. In this regard, a reference artery proximal location PRef is located inside and along the predetermined reference artery Ref and as comparably close to the artery branching point Br as the risk artery proximal location PRsk located inside and along the predetermined risk artery Rsk. On the other hand, a reference artery distal location DRef is a region located outside the predetermined reference artery Ref and as comparably far away from the artery branching point Br as the risk artery distal location DRsk that is also a region located outside the predetermined risk artery Rsk. In this embodiment, all of four data points are determined at the risk artery proximal location PRsk, the risk artery distal region DRsk, the reference artery proximal location PRef, and the reference artery distal region DRef for generating time-density data according to this embodiment.

Figure 6:
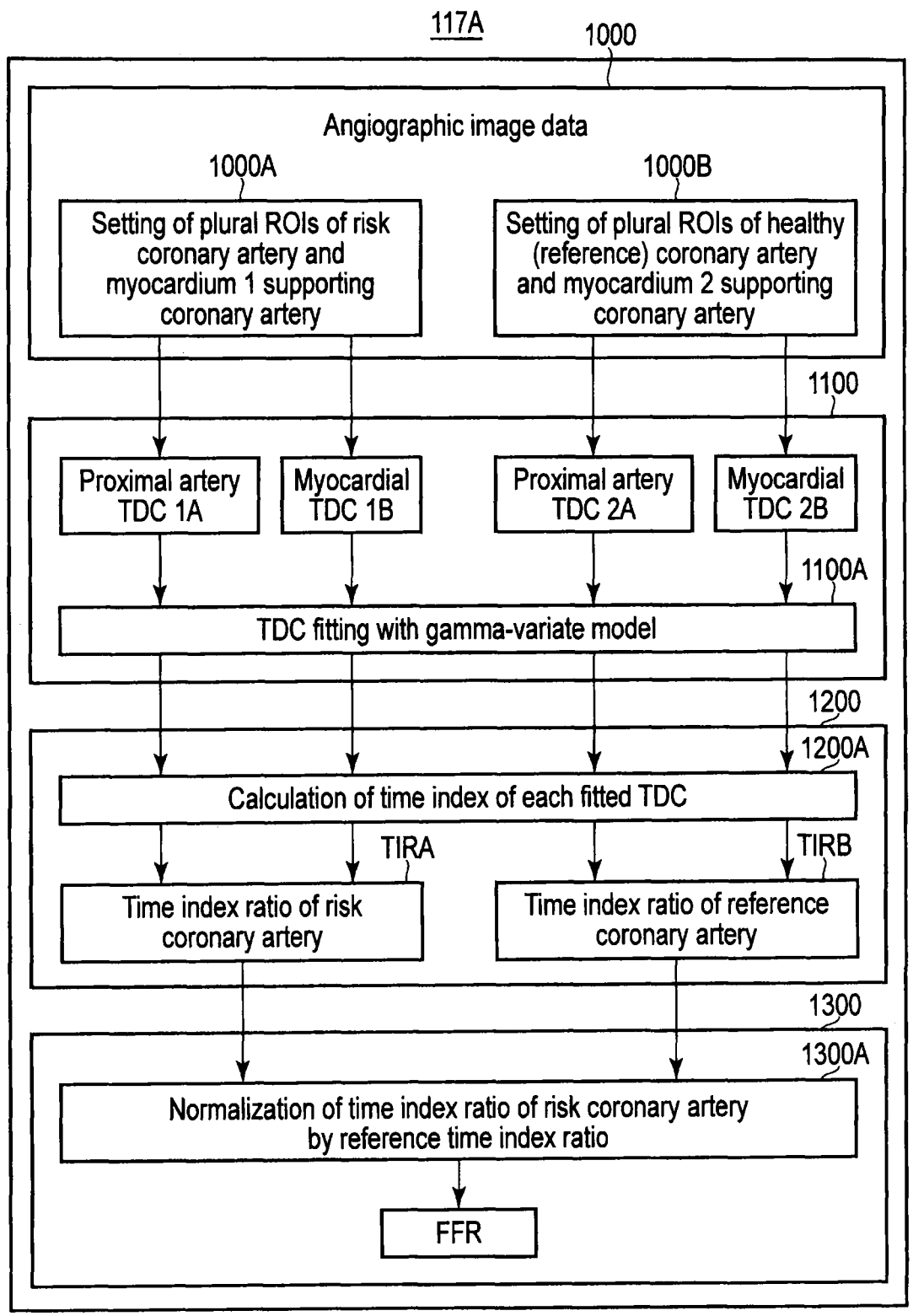
FIG. 6 is a diagram illustrating a blood circulation determining unit according to the embodiment.

Now referring to FIG. 6, a diagram illustrates one embodiment of the blood circulation determining unit 117 according to the current invention. In general, one embodiment of a blood circulation determining unit 117A advantageously determines a predetermined time-based fractional flow reserve (FFR) based upon the angiographic image data that is acquired by a myocardial circulation imaging apparatus. The blood circulation determining unit 117A further includes an angiographic image data initial processing unit 1000 (region setting unit), a time-density curves (TDC) generating unit 1100, a TDC index generating unit 1200, and a time-based fractional flow reserve (FFR) generation outputting unit 1300. In the following description, one embodiment of the blood circulation determining unit 117A determines an FFR based upon the angiographic image data of coronary arteries and a supported myocardium.

In general, a data set of angiographic images is a time sequence of images of a heart blood flow from the entrance of a coronary artery into a myocardium. The angiographic image data include an image before contrast agent injection and images of contrast agent inflow and outflow. All the measurement images are selected at a substantially identical cardiac phase with retrospective cardiac gating. A change in image intensity in contrast agent pixels represents a heart blood flow. Time-density curve measurements of a blood flow are implemented on background subtraction images with motion compensation.

The angiographic image data initial processing unit 1000 extracts a first region of interest (ROI) 1000A including a risk coronary artery and supported myocardium 1 as well as a second region of interest (ROI) 1000B including a healthy or reference coronary artery and supported myocardium 2. The angiographic image data initial processing unit 1000 outputs the extracted image data of the first region of interest (ROI) 1000A and the second region of interest (ROI) 1000B to the time-density curves (TDC) generating unit 1100. The pair of selected arteries generally includes a predetermined risk artery and a predetermined reference artery. The predetermined risk artery is a blood vessel under investigation for suspected stenosis that contributes to some blockage in blood circulation. On the other hand, the predetermined reference artery is a separate blood vessel from the predetermined risk artery and is used as a reference to assure the evaluation for suspected stenosis in the predetermined risk artery. In general, the predetermined reference artery is selected from a group of healthy blood vessels that is comparable in size and location to the predetermined risk artery and is substantially away from stenosis.

The time-density curves (TDC) generating unit 1100 generates four time-density curves. That is, the time-density curves (TDC) generating unit 1100 generates a first pair of a proximal artery TDC 1A and a corresponding myocardial TDC 1B for the risk coronary artery based upon the first region of interest (ROI) 1000A. Similarly, the time-density curves (TDC) generating unit 1100 also generates a second pair of a proximal artery TDC 2A and a corresponding myocardial TDC 2B for the reference coronary artery based upon the second region of interest (ROI) 1000A. The proximal artery TDC 1A is a time-density curve that is generated based upon the time-density data at a proximal artery location that is upstream with respect to suspected stenosis along the risk coronary artery. The corresponding myocardial TDC 1B is a time-density curve that is generated based upon the time-density data at a corresponding distal location that is downstream with respect to the proximal artery location along the risk coronary artery. Similarly, the proximal artery TDC 2A is a time-density curve that is generated based upon the time-density data of the reference artery at a proximal artery location that is comparable to the risk proximal artery location. The corresponding myocardial TDC 2B is a time-density curve that is generated based upon the time-density data at a corresponding distal location that is downstream with respect to the proximal artery location along the reference coronary artery. The time-density curves (TDC) generating unit 1100 further includes a TDC fitting unit 1100A to further process the above four TDCs 1A, 1B, 2A, and 2B with a predetermined fitting model such as gamma-variate model.

The TDC index generating unit 1200 generally calculates a risk ratio (first ratio) based upon selected time indexes. The TDC index generating unit 1200 further includes a time index ratio calculation unit 1200A for selecting a time index of each of the fitted TDCs 1A, 1B, 2A, and 2B and determining a time index ratio based upon the selected time indexes. That is, the TDC index generating unit 1200 selects a time index of a TDC such as a time-to-peak (TTP) index or a mean-transit-time (MTT) index and determines a time value for the selected time index from each of the fitted TDCs 1A, 1B, 2A, and 2B. Subsequently, the time index ratio calculation unit 1200A calculates a time index ratio of the risk coronary artery TIRA based upon the selected index pair in the TDCs 1A and 1B. Similarly, the time index ratio calculation unit 1200A also calculates a time index ratio of the reference coronary artery TIRE based upon the selected index pair in the TDCs 2A and 2B.

Still referring to FIG. 6, the time-based fractional flow reserve (FFR) generation outputting unit 1300 further includes an index ratio normalization unit 1300A for normalizing the risk ratio TIRA (first ratio) by the reference ratio TIRB (second ratio) to determine a time-based fractional flow reserve (FFR) index (stenosis index). Ultimately, the blood circulation determining unit 117A determines the time-based FFR (stenosis index) for evaluating a level of blood circulation between two locations such as the proximal location and the distal location in a selected risk coronary artery with respect to the comparable locations in the selected reference coronary artery. Thus, all of four TDCs 1A, 1B, 2A, and 2B are used to determine a time-based FFR (stenosis index) by the blood circulation determining unit 117A according to this embodiment.

In the above exemplary embodiment, angiographic images are used to illustrate a process in which the time-based FFR (stenosis index) is determined. This exemplary process and embodiment are mere illustrations, and this embodiment is not limited to the use of angiographic image data or the determination of the time-based FFR (stenosis index) for the coronary arteries. This embodiment is applicable to evaluation for blood circulation in blood vessels in various organs.

Figure 7:
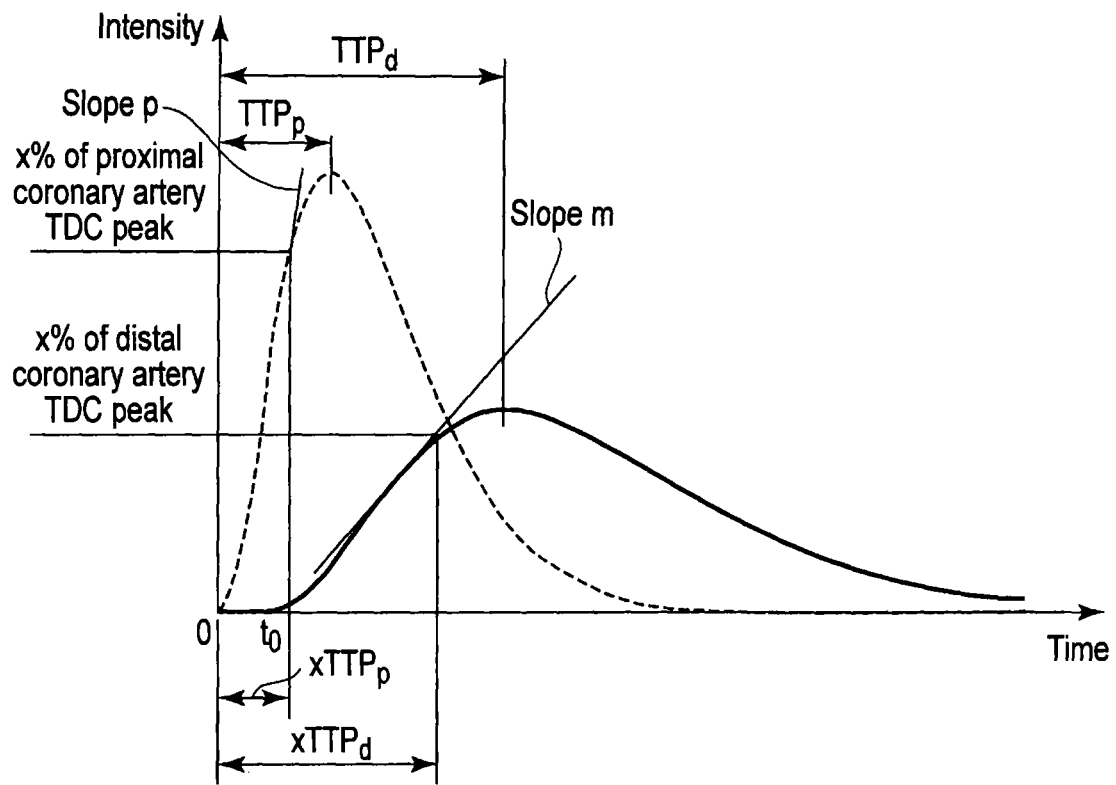
FIG. 7 is a timing chart showing a pair of exemplary time-density curves (TDCs) for illustrating various time indexes to be used in determining the time-based index ratio for evaluating a level of the blood circulation between a proximal location and a distal location in the predetermined risk blood vessel in the region of interest according to the embodiment.

Now referring to FIG. 7, a pair of exemplary time-density curves (TDCs) is provided for illustrating various time indexes to be used in determining the time-based index ratio for evaluating a level of the blood circulation between a proximal location and a distal location in the predetermined risk blood vessel in the region of interest according to this embodiment. The two exemplary TDCs (or TICS (Time-Intensity Curves)) are plotted with the X-axis indicating time and the Y-axis indicating intensity (or density) of a pixel or a group of pixels in a predetermined region of interest (ROI). One of the two exemplary TDCs is a proximal artery TDC based upon intensity measurements at a predetermined proximal location along a predetermined artery, as illustrated in the dotted line. The other of the two exemplary TDCs is a distal artery TDC or myocardial TDC based upon intensity measurements at a predetermined distal location or myocardial location along the predetermined artery, as illustrated in the solid line.

Still referring to FIG. 7, certain time indexes are described with respect to the two exemplary TDCs according to this embodiment. A first exemplary time index is a time-to-peak (TTP). With respect to the proximal artery TDC, its TTP is denoted by $TTP_p$, which indicates an amount of time to reach a peak point in the proximal artery TDC. Similarly, with respect to the distal artery TDC, its TTP is denoted by $TTP_d$, which indicates an amount of time to reach a peak point in the distal artery TDC. Thus, one exemplary time index ratio for a predetermined risk artery is $TTP_p/TTP_d$. A second exemplary time index is a fractional time-to-peak (x×TTP), where x is a predetermined percentage. With respect to the proximal artery TDC, its x×TTP is denoted by x×$TTP_p$, which indicates an amount of time to reach a predetermined percentage of the peak point in the proximal artery TDC. Similarly, with respect to the distal artery TDC, its x×TTP is denoted by x×$TTP_d$, which indicates an amount of time to reach a predetermined percentage of the peak point in the distal artery TDC. Thus, one exemplary time index ratio is (x×$TTP_p$)/(x×$TTP_d$). A third exemplary time index is a mean-transit-time (MTT). Alternatively, an upward slope of the fitted TDC is optionally used as the time index in another embodiment.

With respect to FIG. 7, only one pair of TDCs is illustrated for the sake of simplicity. As discussed above with respect to FIG. 6, all of four TDCs 1A, 1B, 2A, and 2B are used to determine a time-based FFR in the embodiment of the blood circulation determining unit 117A according to this embodiment. In this regard, a second pair of TDCs is optionally plotted in the same graph for a predetermined reference artery. Using the above-described first exemplary time index TTP, with respect to the proximal reference artery TDC, its TTP is denoted by $TTP_{ref\_p}$, which indicates an amount of time to reach a peak point in the proximal reference artery TDC. Similarly, with respect to the distal reference artery TDC, its TTP is denoted by $TTP_{ref\_d}$, which indicates an amount of time to reach a peak point in the distal reference artery TDC. Thus, for the predetermined reference artery, one exemplary time index ratio is $TTP_{ref\_p}/TTP_{ref\_d}$. The above-discussed exemplary time index ratio $TTP_{ref\_p}/TTP_{ref\_d}$ for a predetermined risk artery is thus normalized by the predetermined reference artery time index ratio $TTP_{ref\_p}/TTP_{ref\_d}$ to obtain a time-based fractional flow reserve (FFR) (stenosis index) given by:

$$FFR \cong \frac{TTP_p}{TTP_d} \times \frac{TTP_{ref\_d}}{TTP_{ref\_p}} \quad (1)$$

Note that if a TDC for an extraction fraction of a blood flow to tissues adjacent to the risk distal artery and reference artery is used, $TTP_d$ is replaced by $TTP_m$ and $TTP_{ref\_d}$ is replaced by $TTP_{ref\_m}$. $TTP_m$ indicates an amount of time to reach a peak point in the TDC for the tissue (myocardium) adjacent to the risk distal artery. $TTP_{ref\_m}$ indicates an amount of time to reach a peak point in the TDC for the tissue (myocardium) adjacent to the reference distal artery. To associate the expression obtained by substituting $TTP_m$ and $TTP_{ref\_m}$ into expression (1) with an FFR, the obtained expression is multiplied by the ratio between an extraction ratio from the risk distal artery to the myocardium and that from the reference distal artery to the myocardium.

To account for some of the above characteristics, $$FFR \cong \frac{TTP_p}{TTP_m} \times \frac{TTP_{ref\_m}}{TTP_{ref\_p}} \times \frac{E_{ref\_m}}{E_m} \quad (2)$$

includes an additional term, where $$\frac{E_{ref\_m}}{E_m}$$

is the ratio between the extraction ratios of the myocardium for the reference artery and the risk artery.

The FFR of expression (2) is optionally modified based upon x×TTP as defined by:

$$FFR \cong \frac{x \times TTP_p}{x \times TTP_m} \times \frac{x \times TTP_{ref\_m}}{x \times TTP_{ref\_p}} \times \frac{E_{ref\_m}}{E_m} \quad (3)$$

The FFR is optionally determined based upon MTT as defined by:

$$FFR \cong \frac{MTT_p}{MTT_m} \times \frac{MTT_{ref\_m}}{MTT_{ref\_p}} \times \frac{E_{ref\_m}}{E_m} \quad (4)$$

The FFR is alternatively determined based upon slopes as defined by:

$$FFR \cong \frac{Slope_p}{Slope_m} \times \frac{Slope_{ref\_m}}{Slope_{ref\_p}} \times \frac{E_{ref\_m}}{E_m} \quad (5)$$

The above definition of the fractional flow reserve (FFR) is a ratio that is based upon the assumed relation between a risk artery and a healthy reference artery in a ratio of the blood volume and a ratio of the blood flow time as obtained from the time-density data. The relation is given by:

$$\frac{V_s}{V_p} \times \frac{V_{ref\_d}}{V_{ref\_p}} = \frac{T_{ref\_d}}{T_{ref\_p}} \quad (6)$$

where $V_S$ is a blood volume parameter at a risk artery having stenosis while $V_P$ is a blood volume parameter at a proximal location to the stenosis in the risk artery. $V_{ref\_d}$ is a blood volume parameter at a distal location in a healthy or reference artery while $V_{ref\_p}$ is a blood volume parameter at a proximal location in the healthy or reference artery. Tref_d is a time parameter in the time-density data at a distal location in the healthy or reference artery while $T_{ref\_p}$ is a time parameter in the time-density data at a proximal location in the healthy or reference artery. The reference proximal and distal locations correspond to the proximal and distal locations in the risk artery having stenosis, respectively.

Figure 8:
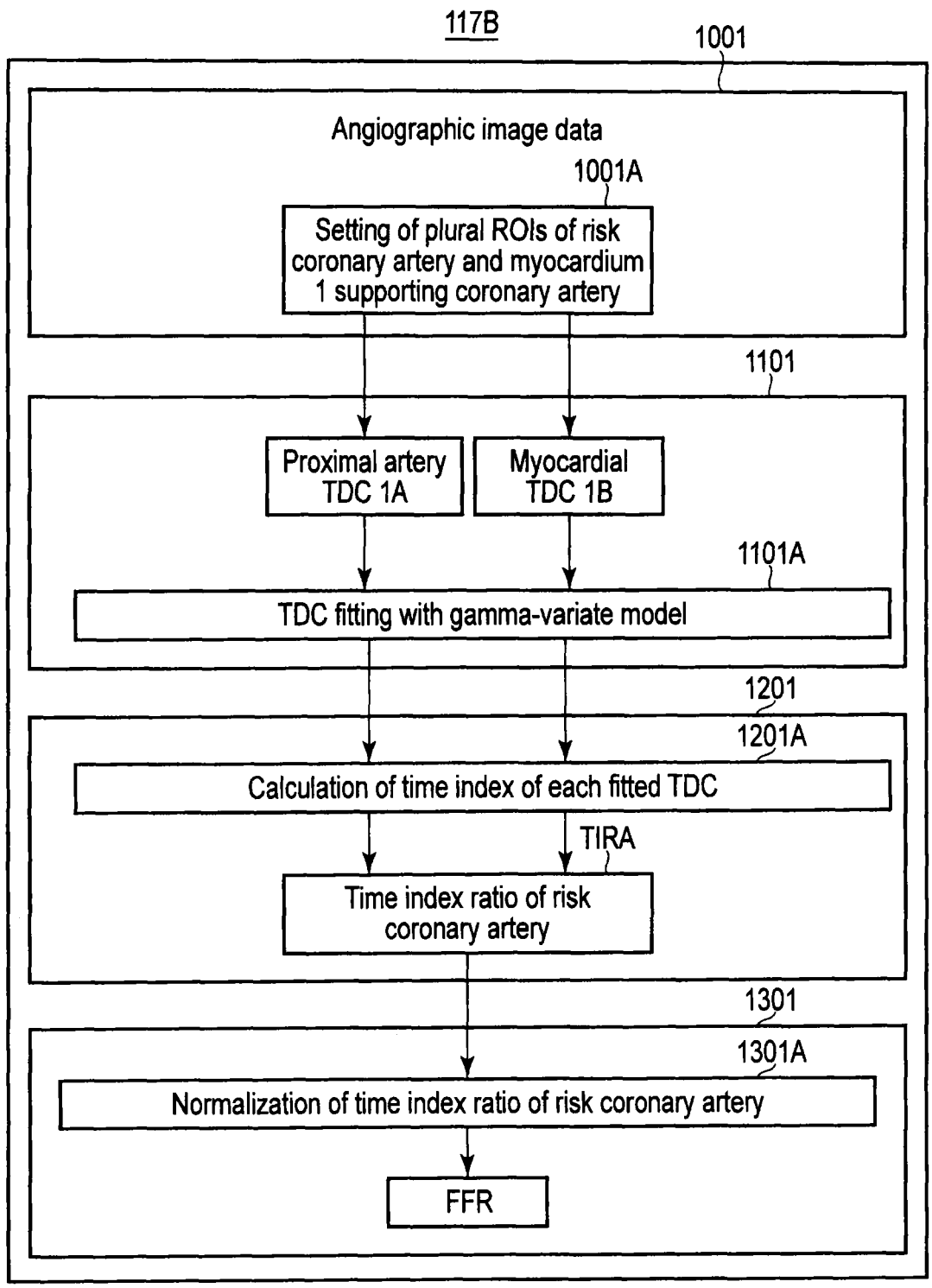
FIG. 8 is a diagram illustrating a blood circulation determining unit according to the embodiment.

Now referring to FIG. 8, a diagram illustrates the second embodiment of the blood circulation determining unit 117 according to the current invention. In general, one embodiment of a blood circulation determining unit 117B advantageously determines a predetermined time-based fractional flow reserve (FFR) (stenosis index) based upon the angiographic image data that is acquired by a myocardial circulation imaging apparatus. The blood circulation determining unit 117B further includes a angiographic image data initial processing unit 1001, a time-density curves (TDC) generating unit 1101, a TDC index generating unit 1201, and a time-based fractional flow reserve (FFR) generation outputting unit 1301. In the following description, one embodiment of the blood circulation determining unit 117B determines an FFR based upon the angiographic image data of coronary arteries and a supported myocardium.

In general, a data set of angiographic images is a time sequence of images of a heart blood flow from the entrance of a coronary artery into a myocardium. The angiographic image data include an image before contrast agent injection and images of contrast agent inflow and outflow. All the measurement images are selected at a substantially identical cardiac phase with retrospective cardiac gating. A change in image intensity in contrast agent pixels represents a heart blood flow. Time-density curve measurements of a blood flow are implemented on background subtraction images with motion compensation.

The angiographic image data initial processing unit 1001 extracts a region of interest (ROI) 1001A including a risk coronary artery and a supported myocardium. The angiographic image data initial processing unit 1001 outputs the extracted image data of the region of interest (ROI) 1001A to the time-density curves (TDC) generating unit 1101. The predetermined risk artery is a blood vessel under investigation for suspected stenosis that contributes to some blockage in blood circulation.

The time-density curves (TDC) generating unit 1101 generates two time-density curves. That is, the time-density curves (TDC) generating unit 1101 generates a pair of a proximal artery TDC 1A and a corresponding myocardial TDC 1B for the predetermined risk coronary artery based upon the region of interest (ROI) 1001A. The proximal artery TDC 1A is a time-density curve that is generated based upon the time-density data at a proximal artery location that is upstream with respect to suspected stenosis along the risk coronary artery. The corresponding myocardial TDC 1B is a time-density curve that is generated based upon the time-density data at a corresponding distal location that is upstream with respect to the proximal artery location along the risk coronary artery. The time-density curves (TDC) generating unit 1101 further includes a TDC fitting unit 1101A to further process the above four TDCs 1A and 1B with a predetermined fitting model such as gamma-variate model.

The TDC index generating unit 1201 generally calculates a ratio based upon selected time indexes. The TDC index generating unit 1201 further includes a time index ratio calculation unit 1201A for selecting a time index of each of the fitted TDCs 1A and 1B, and determining a time index ratio based upon the selected time indexes. That is, the TDC index generating unit 1201 selects a time index of a TDC such as a time-to-peak (TTP) index or a mean-transit-time (MTT) index and determines a time value for the selected time index from each of the fitted TDCs 1A and 1B. Subsequently, the time index ratio calculation unit 1201A calculates a time index ratio of the risk coronary artery TIRA based upon the selected index pair in the TDCs 1A and 1B.

Still referring to FIG. 8, the time-based fractional flow reserve (FFR) generation outputting unit 1301 further includes an index ratio normalization unit 1301A for optionally normalizing the risk ratio TIRA by a predetermined value to determine a time-based fractional flow reserve (FFR) index (stenosis index). Ultimately, the blood circulation determining unit 117B determines the time-based FFR for evaluating a level of blood circulation between two locations such as the proximal location and the distal location in a selected coronary risk artery. Thus, both of two TDCs 1A and 1B are used to determine a time-based FFR in the embodiment of the blood circulation determining unit 117B according to the embodiment.

Now referring to FIGS. 9A through 9G, diagrams illustrate particular examples of the locations where intensity (or density) measurements are taken in order to generate time-density curves according to this embodiment. FIG. 9A illustrates two exemplary locations for taking intensity measurements on the same branch of a blood vessel such as an artery. The two locations on the same branch of the arteries include a proximal location P1 and a distal location D1, and the two locations have a predetermined distance between them along the blood vessel. The time-density curves are generated based upon the time-density data measures at the two locations.

FIG. 9B illustrates exemplary locations for taking intensity measurements on the same branch of a blood vessel such as an artery. The locations on the same branch of the arteries include a proximal location P2 and a predetermined number of distal locations $D2_1$ through $D2_n$, and all of these locations are located inside and along the artery. In one technique, the measurements at the predetermined number of distal locations $D2_1$ through $D2_n$ are collectively used as a second location. The time-density curves are generated based upon the time-density data measures at these two locations.

FIG. 9C illustrates exemplary locations for taking intensity measurements on the same branch of a blood vessel such as an artery. The locations on the same branch of the arteries include a proximal location P3 and a predetermined number of distal locations D3 along a central line of the artery as illustrated in a dotted line, and all of these locations are located inside and along the artery. In one technique, the measurements at the predetermined number of distal locations D3 are collectively used as a second location. The time-density curves are generated based upon the time-density data measures at these two locations.

FIG. 9D illustrates exemplary locations for taking intensity measurements on the same branch of a blood vessel such as an artery. The locations on the same branch of the arteries include a proximal location P4 and a predetermined number of distal locations $D4_1$ through $D4_n$, and all of these locations are located at image pixels outside the artery. In one technique, the measurements at the predetermined number of distal locations $D4_1$ through $D4_n$ are collectively used as a second location. The time-density curves are generated based upon the time-density data measures at these two locations. Note that the second location may be set in all regions except for a stenosis portion and the proximal location P4. Alternatively, the second location may be set for the locations of all the pixels of the angiographic image.

FIG. 9E illustrates exemplary locations for taking intensity measurements on the same branch of a blood vessel such as an artery. The locations on the same branch of the arteries include a proximal location P5 and a predetermined distal tissue area or segment D5 near the artery as illustrated by an enclosed area, and all of these locations are located outside the artery. In one technique, the measurements in the predetermined distal tissue area D5 are collectively used as a second location. The time-density curves are generated based upon the time-density data measures at these two locations.

Figure 9F:
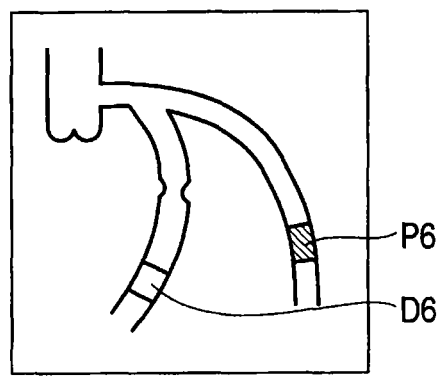
FIG. 9F is a diagram illustrating a sixth pair of exemplary locations for taking intensity measurements on different branches of a blood vessel such as an artery according to the embodiment.

FIG. 9F illustrates two exemplary locations for taking intensity measurements on different branches of a blood vessel such as an artery. The two locations on the two branches of the arteries include a first location P6 and a second location D6, and the two locations have an approximately same distance from the branching point along the blood vessels. In this example, stenosis is illustrated upstream of the first location P6. The time-density curves are generated based upon the time-density data measures at the two locations.

FIG. 9G illustrates three exemplary locations for taking intensity measurements on the same branch of a blood vessel such as an artery and in a tissue segment near the artery. The two locations on the same branch of the arteries include a first location P7 and a second location $D7_1$, and a tissue segment $D7_2$ is located outside the artery near the second location $D7_1$. In this example, stenosis is illustrated upstream of the second location $D7_1$. The time-density curves are generated based upon the time-density data measures at the three locations. Thus, a time-based index ratio (stenosis index) is ultimately determined from a combination of the three TDCs. For example, the time-based index ratio is determined between the time at the proximal vessel location P7 and the distal vessel location $D7_1$. A second example of the time-based index ratio is determined between the distal vessel location $D7_1$ and the distal segment tissue $D7_2$. A third example of the time-based index ratio is determined between the proximal vessel location P7 and the distal segment tissue $D7_2$.

Now referring to FIGS. 10A through 10C, diagrams illustrate a user interface and exemplary displays for the time-based fractional flow reserve (FFR) (stenosis index) values as determined by this embodiment. FIG. 10A illustrates a user interface where the user specifies the input regions among the displayed options 1 through 4. That is, FIG. 10A illustrates FFR (stenosis index) values at locations corresponding to the locations $D2_1$ through $D2_n$ shown in FIG. 9B. FIG. 10B illustrates a user display where the user sees the input region contour that is fused with images. That is, FIG. 10B illustrates FFR (stenosis index) values at locations along the central line shown in FIG. 9C. FIG. 10C illustrates a user display where the user sees numerical values of the new indexes or a map of the new indexes in a region of interest ROI. That is, FIG. 10C may illustrate, for example, FFR (stenosis index) values at locations corresponding to the distal locations $D4_1$ through $D4_n$ shown in FIG. 9D. Note that the second location in FIG. 9D may be set in all the regions except for the stenosis portion and the proximal location P4. Alternatively, the second location may be set for the locations of all the pixels of the angiographic image. In this case, a scalar field indicating a stenosis index as a scalar is displayed as in FIG. 10C. For example, the stenosis index is displayed by shading. The above graphical presentations of the FFR values (stenosis indexes) are merely examples, and this embodiment is not limited to the above examples. For example, in this embodiment, the FFR values (stenosis indexes) are optionally displayed in a predetermined table format.

Now referring to FIG. 11, a flowchart illustrates steps involved in one exemplary process of determining a time-based index ratio (stenosis index) for evaluating blood circulation in a predetermined blood vessel or a predetermined tissue segment according to this embodiment. In step S10 of acquiring angiographic image data, angiographic-related equipment is required to perform the injection of a predetermined contrast agent into the subject S. In further detail, the imaging data (angiographic image data) is not limited to a single view and is optionally obtained from two views. For example, a predetermined contrast agent is injected in bolus into the left ventricular cavity in a coronary study prior to scanning. The detail of a perfusion technique is not going to be described in details here, but well-known angiographic techniques are generally applicable to this embodiment.

In step S20, the blood circulation determination process in the embodiment initially generates time-density data such as time-density curves (TDCs) at predetermined locations along a selected blood vessel from the angiographic image data. The predetermined locations generally include at least a proximal location and a distal location. The proximal location is proximal to a suspected stenosis location in the selected blood vessel and is substantially free from any blockage for blood circulation. On the other hand, the distal location is distal to the suspected stenosis location in the selected blood vessel and is potentially affected by the blockage for blood circulation.

In step S30, one embodiment of the blood circulation determination process further includes steps or actions that are performed by a combination of various software and hardware components. According to one aspect of this embodiment, the blood circulation determination process advantageously determines a predetermined time-based fractional flow reserve (FFR) based upon the angiographic image data that is previously acquired.

Ultimately, the blood circulation determination process determines a predetermined time-based index ratio (stenosis index) such as a time-based FFR for evaluating a level of blood circulation between at least two locations such as the proximal location and the distal location in a selected blood vessel in the region of interest in a step S40. In the evaluation, a certain treatment is considered based upon the time-based index ratio (stenosis index). For example, an FFR threshold value of 0.75 is often used among clinicians although some doctors prefer an FFR threshold value of 0.8. In this regard, a range of the FFR threshold value from 0.75 to 0.8 is considered to be a concerned range where a patient may require medical treatment. The treatment to a patient in the concerned FFR range depends on a totality of a particular patient's conditions. In general, if an FFR value is larger than the clinically accepted FFR threshold value, no serious treatment is generally needed and a patient can go home with some medication. On the other hand, if an FFR value is smaller than the clinically accepted FFR threshold value, a patient generally needs serious medical attention and requires some serious coronary procedure such as surgery.

It is to be understood, however, that even though numerous characteristics and advantages of the embodiment have been set forth in the foregoing description, together with details of the structure and function of the embodiment, the disclosure is illustrative only, and that although changes may be made in detail, especially in matters of shape, size, and arrangement of parts, as well as implementation in software, hardware, or a combination of both, the changes are within the principles of the embodiment to the full extent indicated by the broad general meaning of the terms in which the appended claims are expressed.

As a modification of the above-described embodiment, if the technical idea of the X-ray diagnostic apparatus is implemented by a medical image processing apparatus, as one example, the components surrounded by broken lines in the diagram shown in FIG. 1 are included. In that case, the processing in step Sa1 of this embodiment is replaced by processing of reading out a plurality of time-series medical images from the storage unit 25. Each process in the medical image processing apparatus is the same as that in the embodiment. Furthermore, the medical image processing apparatus can execute the above-described processing by loading a DICOM file (for example, a plurality of time-series medical images (angiographic images)) output from the X-ray diagnostic apparatus or X-ray CT apparatus.

Note that the present invention is not limited to the embodiment intact. The current invention can be embodied by modifying components without departing from the scope of the invention when it is practiced. Also, various inventions can be formed by appropriately combining a plurality of components disclosed in the embodiment. For example, some components may be deleted from all components described in the embodiment. Furthermore, components of different embodiments may be combined as needed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus, comprising:
an X-ray tube configured to generate X-rays;
an X-ray detector configured to detect X-rays generated by the X-ray tube and transmitted through a subject; and
processing circuitry configured to
generate a plurality of time series medical images of vasoganglion in a coronary artery of the subject based on an output from the X-ray detector,
receive a setting of a first upstream region and a first downstream region on each of the plurality of time series medical images with respect to a stenosis location in a first blood vessel in the vasoganglion, the first upstream region being upstream of the stenosis location and on the first blood vessel, the first downstream region being downstream of the stenosis location,
generate a stenosis upstream curve indicating a change in pixel value over time based on a plurality of pixel values included in the first upstream region set on the first blood vessel in each of the plurality of time series medical images, and generate a stenosis downstream curve indicating a change in pixel value over time based on a plurality of pixel values included in the first downstream region,
generate a stenosis index indicating a degree of stenosis in the first blood vessel based on the stenosis upstream curve and the stenosis downstream curve, the stenosis index corresponding to a fractional flow reserve (FFR), and
cause a display to display the stenosis index,
wherein the processing circuitry is further configured to generate the stenosis index based on a ratio of a first length of time to a second length of time, the first length of time being from a start timing to a timing of a peak value on the stenosis upstream curve, and the second length of time being from the start timing to a peak value on the stenosis downstream curve.

2. The X-ray diagnostic apparatus according to claim 1, wherein:
the processing circuitry is further configured to receive a setting of a second upstream region corresponding to the first upstream region and a second downstream region corresponding to the first downstream region, in a non-stenotic second blood vessel in the vasoganglion, based on a branching portion of the first blood vessel and the second blood vessel;
the processing circuitry is further configured to generate a non-stenosis upstream curve indicating a change in pixel value over time based on a plurality of pixel values included in the second upstream region, and generates a non-stenosis downstream curve indicating a change in pixel value over time based on a plurality of pixel values included in the second downstream region; and
the processing circuitry is further configured to generate an additional stenosis index based on the first length of time, the second length of time, a third length of time from a start timing to a timing of a peak value on the non-stenosis upstream curve, and a fourth length of time from a start timing to a timing of a peak value on the non-stenosis downstream curve.

3. The X-ray diagnostic apparatus according to claim 2, wherein the processing circuitry is further configured to generate, as the additional stenosis index, a normalized ratio obtained by normalizing a first ratio of the first length of time to the second length of time by a second ratio of the third length of time to the fourth length of time.

4. The X-ray diagnostic apparatus according to claim 2, wherein:
the processing circuitry is further configured to receive a setting of a first tissue region adjacent to the first downstream region and a second tissue region adjacent to the second downstream region, and the processing circuitry is further configured to
generate the stenosis downstream curve based upon a plurality of pixel values included in the first tissue region,
generate the non-stenosis downstream curve based upon a plurality of pixel values included in the second tissue region, and
generate an additional stenosis index based on a first extraction ratio indicating a ratio of a blood volume extracted from the first downstream region to the first tissue region, a second extraction ratio indicating a ratio of a blood volume extracted from the second downstream region to the second tissue region, the first length of time, the second length of time, the third length of time, and the fourth length of time.

5. The X-ray diagnostic apparatus according to claim 1, wherein the processing circuitry is further configured to
generate the medical images corresponding to a first projection direction and a second projection direction different from the first projection direction for the subject, and
generate an additional stenosis index based on the first length of time and the second length of time corresponding to the first projection direction and the first length of time and the second length of time corresponding to the second projection direction.

6. The X-ray diagnostic apparatus according to claim 1, wherein:
the processing circuitry is further configured to receive a setting of a first tissue region adjacent to the first downstream region;
the processing circuitry is further configured to generate the stenosis downstream curve based on a plurality of pixel values included in the first tissue region; and
the processing circuitry is further configured to generate an additional stenosis index based on the first length of time, the second length of time, and a first extraction ratio indicating a ratio of a blood volume extracted from the first downstream region to the first tissue region.

7. A medical image processing apparatus, comprising:
a memory to store a plurality of time series medical images of vasoganglion in a coronary artery of a subject; and
processing circuitry configured to
receive a setting of a first upstream region and a first downstream region on each of the plurality of time series medical images with respect to a stenosis location in a first blood vessel in the vasoganglion the first upstream region being upstream of the stenosis location and on the first blood vessel, the first downstream region being downstream of the stenosis location,
generate a stenosis upstream curve indicating a change in pixel value over time based on a plurality of pixel values included in the first upstream region set on the first blood vessel in each of the plurality of time series medical images, and generate a stenosis downstream curve indicating a change in pixel value over time based on a plurality of pixel values included in the first downstream region,
generate a stenosis index indicating a degree of stenosis in the first blood vessel based on the stenosis upstream curve and the stenosis downstream curve, the stenosis index corresponding to a fractional flow reserve (FFR), and
cause a display to display the stenosis index,
wherein the processing circuitry is further configured to generate the stenosis index based on a ratio of a first length of time to a second length of time, the first length of time being from a start timing to a timing of a peak value on the stenosis upstream curve, and the second length of time being from the start timing to a peak value on the stenosis downstream curve.

\* \* \* \* \*